(12) United States Patent
Bauer

(10) Patent No.: US 8,821,875 B2
(45) Date of Patent: Sep. 2, 2014

(54) PHARMACEUTICAL COMPOSITION COMPRISING ANTIBODIES AGAINST CATALASE AND SUPEROXIDE DISMUTASE FOR TUMOR THERAPY

(75) Inventor: Georg Bauer, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 14/119,177

(22) PCT Filed: Jun. 15, 2012

(86) PCT No.: PCT/EP2012/061393
§ 371 (c)(1),
(2), (4) Date: Nov. 20, 2013

(87) PCT Pub. No.: WO2012/172034
PCT Pub. Date: Dec. 20, 2012

(65) Prior Publication Data
US 2014/0099327 A1 Apr. 10, 2014

(30) Foreign Application Priority Data

Jun. 16, 2011 (EP) .................................... 11170076

(51) Int. Cl.
*A61K 39/395* (2006.01)
*C07K 16/40* (2006.01)
*C07K 16/30* (2006.01)
*A61K 39/00* (2006.01)

(52) U.S. Cl.
CPC .......... *A61K 39/39558* (2013.01); *C07K 16/40* (2013.01); *C07K 16/30* (2013.01); *A61K 2039/507* (2013.01)
USPC .................. 424/146.1; 424/155.1; 424/174.1; 424/130.1; 424/138.1

(58) Field of Classification Search
CPC .................. A61K 2039/507; A61K 39/39558; C07K 16/30; C07K 16/40
See application file for complete search history.

(56) References Cited

FOREIGN PATENT DOCUMENTS

EP  0 349 113 A1  1/1990

OTHER PUBLICATIONS

Heinzelmann, Sonja et al., "Multiple protective functions of catalase against intercellular apoptosis-inducing ROS signaling of human tumor cells", Biol. Chem., Jun. 2010, vol. 391, pp. 675-693.
Bechtel, Wibke et al., "Catalase protects tumor cells from apoptosis induction by intercellular ROS signaling", Anticancer Research, Nov. 2009, vol. 29 (11), pp. 4541-4558.
Bechtel, Wibke et al., "Modulation of Intercellular ROS Signaling of Human Tumor Cells", Anticancer Research, Nov. 2009, vol. 29 (11), pp. 4559-4570.
Mates, JM et al., "Role of reactive oxygen species in apoptosis: implications for cancer therapy", Intl J. of Biochem and Cell. Biol., Feb. 2000, vol. 32 (2), pp. 157-170.
Van Driel, BEM et al., "Expression of CuZn- and Mn-Superoxide Dismutase in Human Colorectal Neoplasms", Free Radical Biology and Medicine, Jan. 1997, vol. 23(3), pp. 435-444.
Iwase, K. et al., "Cu/Zn- and Mn-Superoxide Dismutase Distribution and Concentration in Adrenal Tumors", J. of Surgical Research, Sep. 2006, vol. 135 (1), pp. 150-155.
Meents, M., "Spoptoseinduktion mittels ROS-/RNS-Signalling bei Leukamie- und Lymphonzellen im Vergleich zu EBV-immortalisierten Lymphozyten", Inaugural Dissertation, Albert-Ludwigs-Universitaet Freiburg Im Breisgau, Jan. 2009, pp. 1-156.

*Primary Examiner* — Daniel C Gamett
(74) *Attorney, Agent, or Firm* — Chalin A. Smith; Smith Patent

(57) ABSTRACT

The present invention is based on the unexpected finding that, in addition to catalase, SOD is also involved in protecting tumor cells, wherein the inhibition effects of the two protective enzymes support one another in a complementary manner. The invention thus relates to pharmaceutical compositions containing at least two antibodies or the biologically active fragments thereof, wherein the one antibody is directed against the catalase and the other antibody is directed against the superoxide dismutase, as well as their use for treating a tumor disease.

6 Claims, 20 Drawing Sheets

PHARMACEUTICAL COMPOSITION COMPRISING ANTIBODIES AGAINST CATALASE AND SUPEROXIDE DISMUTASE FOR TUMOR THERAPY

PRIORITY

This application corresponds to the national phase of International Application No. PCT/EP2012/061393 filed Jun. 15, 2012 which, in turn, claims priority to European Patent Application No. 11.170076.1 filed Jun. 16, 2011, the contents of which are incorporated by reference herein in their entirety.

FIELD OF THE PRESENT INVENTION

The present invention relates to pharmaceutical compositions containing at least two antibodies or the biologically active fragments thereof, wherein the one antibody is directed against the catalase and the other antibody is directed against the superoxide dismutase, as well as their use for treating a tumor disease.

BACKGROUND OF THE PRESENT INVENTION

Malignant cells are characterized by the extracellular production of superoxide anions by membranous NADPH oxidase (NOX-1). Here, the activity of NOX is controlled by oncogenes such as e.g., RAS by involving RAC. The superoxide anions generated by malignant cells and their dismutation product hydrogen peroxide are essential for the proliferation of these cells and for the maintenance of their transformed state (Heinzelmann and Bauer, Biol. Chem., Vol. 391, 2010, p. 675-693).

However, the other side of the coin from the extracellular production of reactive oxygen species (ROS) is the formation of intercellular ROS-mediated signal paths selectively directing themselves against cells with the transformed phenotype. These are the main paths shown in FIG. 1, namely the HOCl and the NO/peroxynitrite signal path as well as two further paths of secondary importance, namely the nitryl chloride path and the metal catalyzed Haber-Weiss reaction that are not considered in the illustration. In the course of the tumor progression tumor cells acquire resistance against the intercellular ROS signal paths by expressing catalase on their cell membrane. This inhibits the HOCl and the nitryl chloride path as well as the metal catalyzed Haber-Weiss reaction by converting hydrogen peroxide into water and oxygen, and counteracts the NO/peroxynitrite path by decomposing peroxynitrite and oxidizing NO to $NO_2$ with the help of its active intermediate compound I, and so prevents the formation of peroxynitrite.

Abolishing the catalase-mediated protection of tumor cells represents an attractive concept for the development of a novel form of tumor therapy that is specifically directed against cells with the malignant phenotype (due to the features of membranous catalase and superoxide anion production) and does not endangers normal cells, since these neither produce extracellular superoxide anions nor express membranous catalase.

SUMMARY OF THE PRESENT INVENTION

The present invention is based on the unexpected finding that, in addition to catalase, SOD is also involved in protecting tumor cells, wherein the inhibition effects of the two protective enzymes support one another in a complementary manner.

The application of monoclonal antibodies or Fab fragments against catalase or SOD reactivates intercellular ROS signaling and leads to the apoptosis of the cells. It is shown that with the inhibition of one of the two enzymes inevitably by the biochemical consequences induced this way in the area of the cell membrane also the complementary protective partner is inevitably inhibited.

Unexpected and of high therapeutic value is the finding that antibodies or Fab fragments against SOD and catalase cooperate synergistically. On this basis, a specific form of the synergistic antibody therapy is disclosed.

DETAILED DESCRIPTION OF THE PREFERRED EMBODIMENTS

Figure 1:
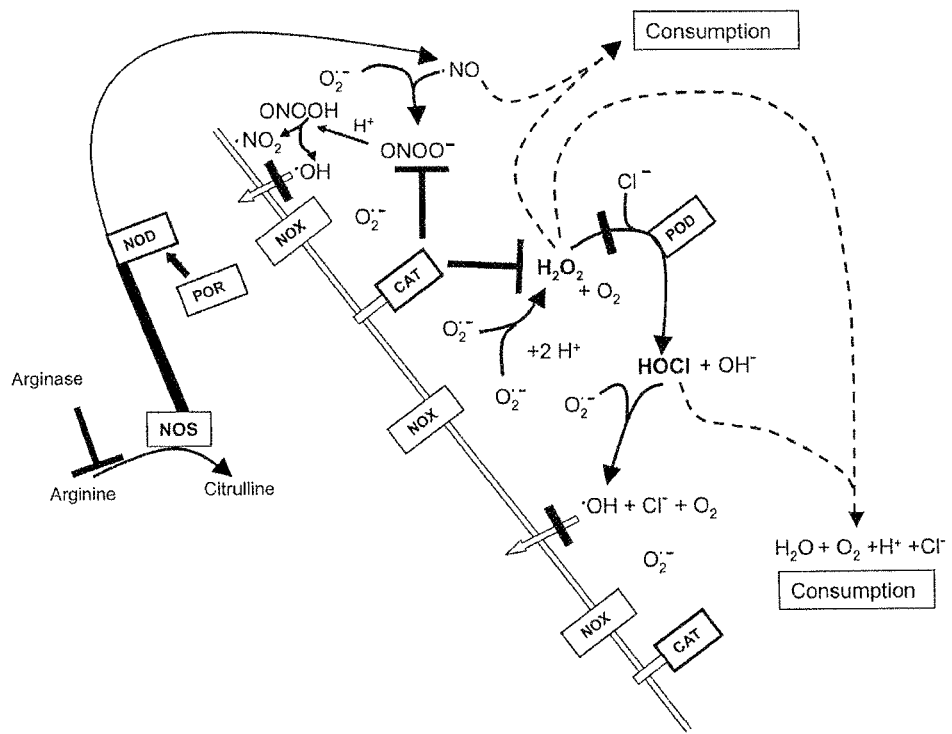
FIG. 1 depicts the mechanism by which tumor cells are protected against intercellular ROS signaling by membranous catalase (CAT). The illustration on the left the intracellular, on the right the intercellular area of a tumor cell and between them that with the potential intercellular ROS signaling.

The considerations underlying the present invention are explained in more detail in FIGS. 1 to 6 and the following explanations:

Figure Legends:
Legend to Scheme 1 (FIG. 1)

Tumor cells are protected by membranous catalase (CAT) against intercellular ROS signaling The illustration on the left shows the intracellular, on the right the intercellular area of a tumor cell and between them that with the potential intercellular ROS signaling. In the cell membrane there is the activated NADPH oxidase NOX-1 that generates superoxide anions extracellulary. These spontaneously dismutate to hydrogen peroxide and oxygen. The cells release peroxidase (POD) that is encoded by DUOX (not shown) and cleaved off by matrix metalloproteases. Hydrogen peroxide is converted by the free peroxidase (POD) to HOCl that reacts with superoxide anions to apoptosis-inducing hydroxyl radicals. With a relative excess of hydrogen peroxide the consumption reaction of HOCl occurs that weakens the HOCl path. NO synthase (NOS) generates NO that is either consumed by hydrogen peroxide in a complex consumption reaction or reacts with superoxide anions to peroxynitrite. After the formation of peroxynitrite acid and its decomposition into hydroxyl radicals and $NO_2$ the induction of apoptosis occurs. The two secondary signal pathways nitryl chloride pathway and metal catalyzed Haber-Weiss reaction are not considered in the scheme. The concentration of NO that is available in the system depends on the arginine concentration, the concentration of arginase, and the influence of NO dioxygenase (NOD), among others. In turn, NOD is associated with cytochrome P 450-dependent oxidoreductase (POR). The NOD/POR complex diminishes the NO concentration by its conversion into nitrate.

It is of particular importance that the target cell function "formation of superoxide anions" is strictly associated with the transformed phenotype and is highly selective. It is controlled by activated oncogenes. However, the effector functions "release of peroxidase" and "NO release" can be performed both by not-transformed and transformed cells themselves. That's why intercellular ROS signaling goes both in the interaction between transformed and not-transformed cells (classical intercellular induction of apoptosis) and also in an autocrine manner between transformed cells (as shown in this illustration).

Tumor cells on their outer surface bear sufficient membranous catalase that destroys hydrogen peroxide and thus inhibits the HOCl pathway (as well as the not shown nitryl chloride pathway and the metal catalyzed Haber-Weiss reaction). Moreover, catalase also destroys peroxynitrite and thus effectively interferes with the NO/peroxynitrite pathway. For reasons of clarity, a second negative interaction of the catalase with the NO/peroxynitrite pathway is not shown: Compound I of the catalase can oxidize NO to $NO_2$ and thus inhibit the NO/peroxynitrite pathway.

The inhibition of the catalase by an antibody reaction results in the reactivation of the shown ROS signal pathways and subsequently in apoptosis.

The object of this patent application is a synergistic effect with the participation of SOD that is described in more detail in the following figure.

Figure 2:
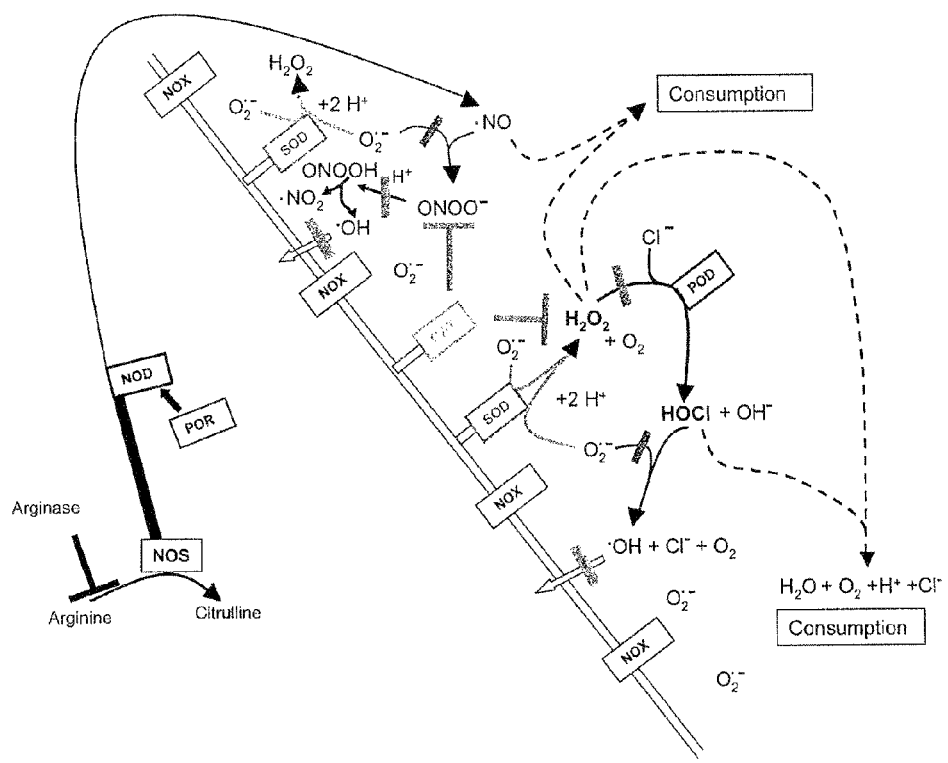
FIG. 2 depicts a theoretical reaction scheme demonstrating the synergy of catalase and SOD in the protection of tumor cells against intercellular ROS signaling.

Legend to Scheme 2 (FIG. 2)

Without wishing to be bound by any theory the synergy of catalase and SOD in the protection of tumor cells against intercellular ROS signaling could be based on the following considerations:

Since also specific antibodies against SOD result in the re-establishment of the ROS signaling the conclusion is justified that also SOD is present on the surface of the tumor cells. It can be seen that SOD and catalase complement and enhance one another in their protective effect. So, SOD by converting free superoxide anions to hydrogen peroxide prevents the formation of peroxynitrite from NO and superoxide anions, whereas catalase can degrade possibly formed peroxynitrite. In this way, the NO/peroxynitrite pathway is secured twice. By degrading hydrogen peroxide catalase prevents the synthesis of HOCl, whereas SOD prevents superoxide anions from interacting with possibly formed HOCl and thus apoptosis-inducing hydroxyl radicals from being formed. Thus, also the HOCl pathway is secured twice by SOD and catalase. For reasons of clarity, further protective mechanisms of secondary importance are not mentioned. These are the oxidation of NO to $NO_2$ that occurs by compound I of the catalase (CAT $Fe^{IV}=O^+$) and the destruction of peroxynitrite by SOD (wherein nitronium ions and water are formed).

However, the scheme does not provide any way to explain the observation made that both the inhibition of the catalase and the inhibition of the SOD result in the induction of apoptosis. This is discussed in more detail in the reaction schemes of FIGS. 3-6.

Thus, object of the present patent application are pharmaceutical compositions that are characterized in that they contain at least two different antibodies or their biologically active fragments, wherein one of these antibodies is directed against the catalase and the other antibody is directed against the superoxide dismutase.

Within the scope of the present invention especially monoclonal antibodies are employed that are preferably present either in a humanized form or more preferably in a completely human form.

The production of monoclonal antibodies is known since the fundamental works of Köhler and Milstein. The application of monoclonal antibodies recovered within the scope of the mouse hybridoma technology are only very limitedly suited for pharmaceutical use. The reason for this is that with the repeated application in humans antibodies against the skeleton components of the antibodies encoded by mouse genes originate. Thus, such antibodies are preferably humanized. Here, the skeleton parts of the antibodies encoded by mouse genes are replaced by human gene sequences. Here the problem is that the specificity and affinity of the antibodies are often deteriorated.

In a particularly preferred embodiment the antibodies according to the invention are produced with the help of the so-called PHAGE display technology. Here, antibodies originate that are completely built up from human sequences and thus in application do not produce antibodies against these antibodies.

It is important in the production of the antibodies that the antigen against which the antibodies are directed is presented in a form that corresponds closely to the situation in vivo. Thus, for the production of the antibodies suitable cells or cell preparations can be used that present the spatial configuration of the antigens (here, catalase and superoxide dismutase, respectively) in a form that corresponds closely to the native form.

The antibodies employed according to the invention can be directed against the two antigens (catalase and superoxide dismutase), wherein these may be epitopes that are localized on these two enzymes. In a particularly preferred embodiment the antibodies bind to the catalytic centers of the two enzymes catalase and superoxide dismutase, respectively. It is also possible that the epitopes are localized in the vicinity of the catalytic centers. Due to the size of the antibodies it is often sufficient that the antibodies bind in the vicinity of the catalytic centers because in this way the access of the substrate to the enzyme is prevented.

By the term "antibodies or their binding parts" there are not only understood complete antibodies of the various antibody classes, in particular IgM, IgA, and particularly preferred IgG. Instead, they can also only be the binding fragments, the so-called Fab fragments specifically binding to the epitopes.

In a further embodiment of the present invention it is possible to couple two Fab fragments to so-called diabodies, wherein the one Fab fragment binds to the catalase and the other Fab fragment to the superoxide dismutase. With this coupling a particularly high efficacy can be achieved.

The pharmaceutical compositions according to the invention containing on the one hand an antibody or binding fragments thereof, respectively, directed against catalase and on the other hand an antibody or binding fragments thereof, respectively, directed against the superoxide dismutase are preferably employed in the therapy of tumor diseases. A particularly good efficacy was observed in the following tumor diseases: carcinomas, in particular of the stomach; Ewing's sarcomas, neuroblastomas, cervical carcinomas.

The following experiments were performed with the following antibodies or Fab fragments, respectively:

(1) Monoclonal antibody (mouse; IgG1) against human catalase (Clone CAT-505) (Charge number: 088K4809). Manufacturer Sigma Aldrich, Schnelldorf, Germany.

2) Monoclonal antibody (mouse, IgG1) against human SOD-1 (Clone SD-G6) (Charge number 035K4823). Manufacturer Sigma Aldrich, Schnelldorf, Germany.

3) Recombinant human Fab fragments against human catalase, Format Fab-V5Sx2, produced by AbDSerotec from a HuCAL® Library (protected by EP 859841; U.S. Pat. No. 6,300,064; U 725609). The fragments employed were #AbD15562 and #AbD15563 with catalase inhibition effect and fragment AbD15558 that binds to catalase, but does not inhibit it.

4) Recombinant human Fab fragments against human SOD, Format Fab-V5Sx2, produced by AbDSerotec from a HuCAL® Library. The fragments employed were #AbD15660 and #AbD15662 with SOD inhibition effect and fragment AbD15661 that binds to SOD, but does not inhibit it. The abbreviations given in the following list have been used:

LIST OF ABBREVIATIONS

AEBSF 4-(2-aminoethyl)-benzenesulfonyl fluoride
  (inhibitor of the NADPH oxidase)
ABH 4-aminobenzoyl hydrazide
  (peroxidase inhibitor)
3-AT 3-aminotriazole
  (catalase inhibitor)
aCAT antibody against catalase
aSOD antibody against SOD
3-Br-7-NI 3-bromo-7-nitroindazole
  (selective inhibitor for neuronal NOS (nNOS))
CAT catalase
Compound I activated intermediate stage of catalase of formula
  CAT $Fe^{IV}=O^+$. Compound I is formed in the reaction of catalase with a molecule hydrogen peroxide or peroxynitrite.
DEA NONOate 2-(N,N-diethylamino)-diazenolate-2-oxide. diethylammonium salt
  (rapidly decomposing NO donor)
Duox dual oxidase
  (membranous enzyme consisting of a NADPH oxidase and a peroxidase domain. The peroxidase domain is cleaved off with the help of proteases.)
EUK 134 chloro[[2,2'-[1,2-ethanediylbis[(nitrilo-κN)methylidyne]]bis[6-methoxyphenolato-κO]]]-manganese)
  (catalase mimetic)
FBS fetal bovine serum
FeTPPS 5-, 10-, 15-, 20-tetrakis(4-sulfonatophenyl)porphyrinato iron(III) chloride
  (peroxynitrite decomposition catalyst)
MnTE-2PyP Mn(III) meso-tetrakis(N-ethyl-2-pyridyl)porphyrin pentachloride
  (cell-permeable SOD mimetic)
L-NAME N-ω-nitro-L-arginine methylester hydrochloride
  (NOS inhibitor)
NO nitric oxide
NOD nitric oxide dioxygenase (oxidizes NO to nitrate)
NOS NO synthase
NOX NADPH oxidase (here, in particular the membranous NOX-1)
POD peroxidase
  (in this context in particular the ability of certain peroxidases takes effect that in the presence of hydrogen peroxide they are able to oxidize chloride to HOCl)
PON peroxynitrite
POR cytochrome P 450 oxidoreductase
RAS, RAC oncogenes
ROS reactive oxygen and nitrogen species
  (radical and non-radical species such as superoxide anions, hydroxyl radicals, nitric oxide, hydrogen peroxide, HOCl, peroxynitrite, etc.)
siRNA small interfering RNA
  (reagent to specifically down-regulate the synthesis of defined gene products)
SOD superoxide dismutase (here, in particular SOD-1 (Cu$^{++}$ in the active center of the tumor cells and MnSOD from bacteria for analytical purposes)
TGF-beta transforming growth factor type beta

EXAMPLES

In the scope of the present invention there have been made experiments with experimental results being shown in FIGS. 7 to 20.

Example 1

Specific Sensitization of Tumor Cells for Apoptosis-Inducing ROS Signaling by Antibodies Against Catalase To 12 500 MKN-45 cells in 100 ml RPMI 1640 medium, 10% FBS the given concentrations of the monoclonal antibodies against catalase, EGF receptor, elastin, fibronectin, or laminin were added and the incubation was continued for 4 hours at 37° C., 5% CO$_2$. Then, the percentage of apoptotic cells (duplicates) was determined according to the classical apoptosis criteria membrane blebbing, nuclear condensation, and/or nuclear fragmentation.

Figure 7:
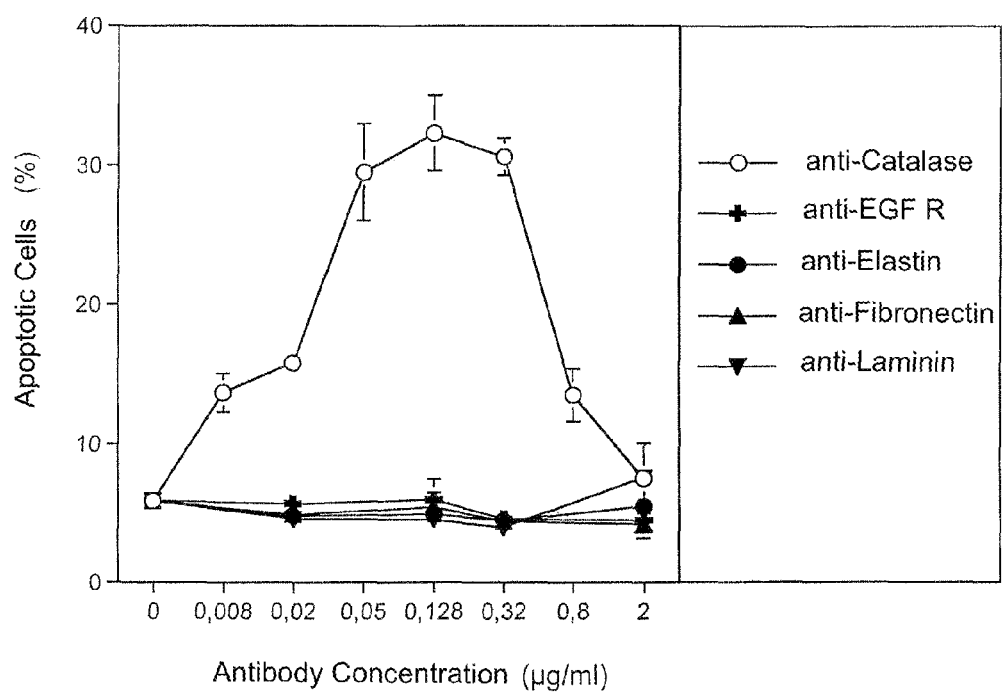
FIG. 7 depicts the specific induction of apoptosis in MKN-45 gastric carcinoma cells by monoclonal antibodies against catalase.

FIG. 7 shows that antibodies against catalase, but not antibodies directed against other membrane-associated proteins induce apoptosis in the tumor cells, wherein the effect is represented in the form of an optimum curve as it has been also described in the work of Heinzelmann and Bauer, 2010 for the catalase inhibitor 3-aminotriazole.

The addition of monoclonal antibodies against human catalase in the gastric carcinoma cell line MKN-45 results in the induction of apoptosis. This sensitization has the form of an optimum curve with respect to the concentration of the antibodies. The specificity of the induced process is shown by the fact that monoclonal antibodies against a number of other membrane structures of the tumor cells such as e.g. EGF receptor, elastin, fibronectin, or laminin do not result in the induction of apoptosis (FIG. 7). For sensitization it is also not sufficient that antibodies bind to a membranous structure. Specific binding to catalase resulting in an obvious inhibition of the function of the catalase seems to be indispensable for the sensitization.

To 12 500 MKN-45 cells in 100 ml RPMI 1640 medium, 10% FBS the given concentrations of the monoclonal antibodies against catalase as well as the mentioned inhibitors were added and the incubation was continued for 2 hours at 37° C., 5% CO$_2$, before in duplicates the percentages of apoptotic cells were determined.

Inhibitors: 50 mM caspase-3 inhibitor; 25 mM caspase-9 inhibitor, 100 μM AEBSF (NADPH oxidase inhibitor), 120 U/ml MnSOD, 2.4 mM L-NAME (NOS inhibitor); 40 mM FeTPPS (peroxynitrite decomposition catalyst); 150 mM 4-aminobenzoylhydrazide (ABH) (peroxidase inhibitor); 50 mM taurine (HOCl scavenger).

Figure 8:
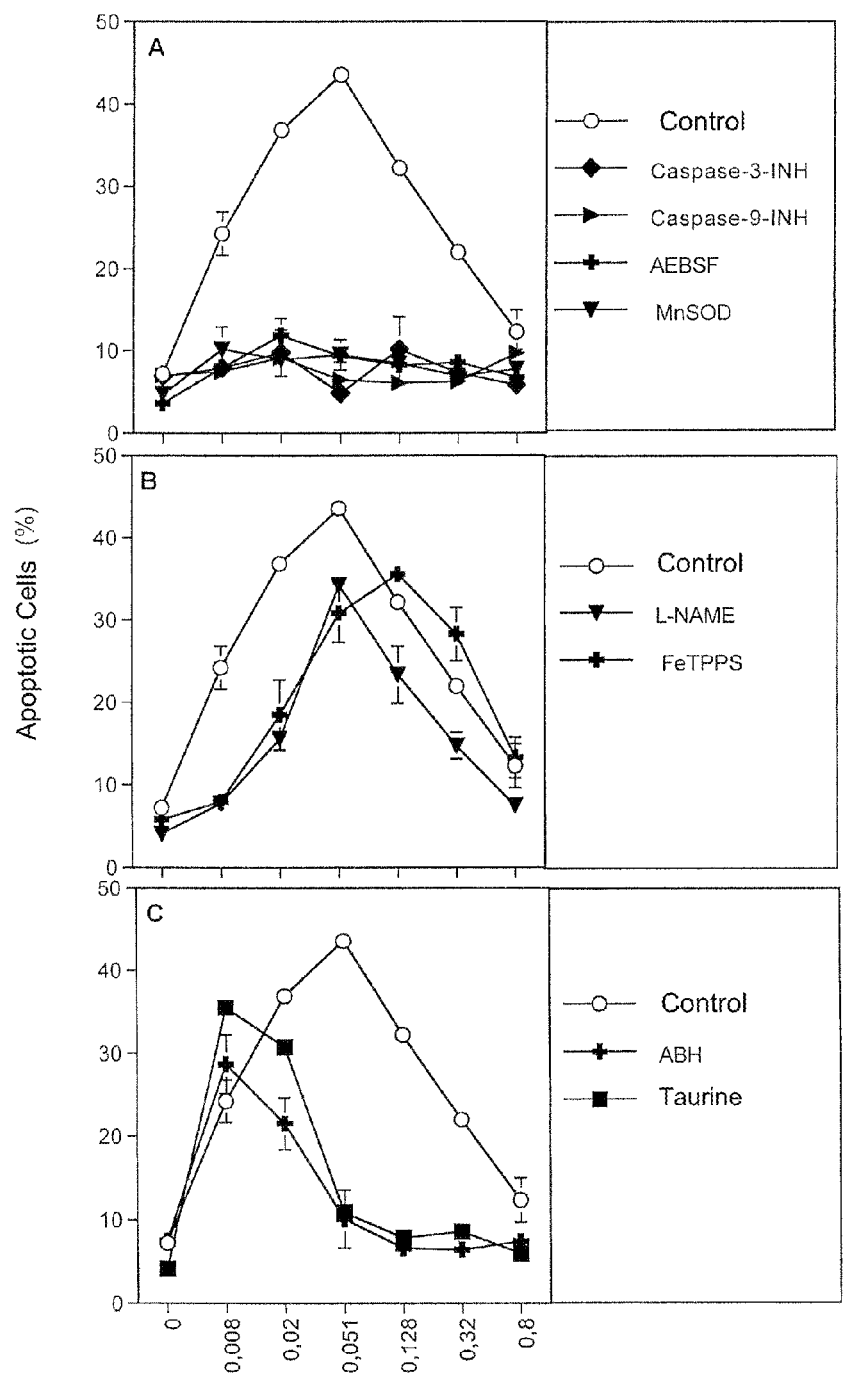
FIG. 8, parts A-C, demonstrate that the induction of apoptosis in tumor cells by anti-catalase antibodies is based on the re-establishment of the intercellular ROS signaling.

FIG. 8 shows that the induction of apoptosis in MKN-45 cells is performed after application of a monoclonal antibody against catalase by caspase-9 and caspase-3. The induction of apoptosis in the entire concentration range of the antibody depends on superoxide anions that in the lower concentration range of the antibody drive the NO/peroxynitrite pathway, in the higher concentration range the HOCl pathway.

FIG. 8 shows that this assumption is right and that the inhibition of the catalase by antibodies in fact is of functional importance for the induction of the intercellular apoptosis. The concentration dependent induction of apoptosis in MKN-45 cells by a monoclonal antibody against catalase is inhibited by AEBSF (4-(2-aminoethyl)benzene-sulfonyl fluoride), an inhibitor of the superoxide anions-producing NADPH oxidase, and by SOD. This proves that the induction of apoptosis in the entire concentration range of the antibody depends on superoxide anions. Due to the inhibitory effect of the non-cell permeable SOD it is made clear that these must be extracellular superoxide anions. The complete inhibition of the apoptosis by caspase-9 and caspase-3 inhibitors proves that the mitochondrial pathway of the apoptosis is running. The apoptosis induced by the antibody against catalase is inhibited in the lower concentration range of the antibody by L-NAME (N-ω-nitro-L-arginine methylester hydrochloride), an inhibitor of the NO synthase, and by FeTPPS (5-,10-,15-,20-tetrakis(4-sulfonatophenyl)porphyrinato iron(III) chloride), an peroxynitrite decomposer what indicates to the role of the NO/peroxynitrite pathway. With a higher antibody concentration the NO/peroxynitrite pathway is replaced by the HOCl pathway as can be seen from the inhibitory effect of the peroxidase inhibitor 4-amino-benzoylhydrazide (ABH) and the HOCl scavenger taurine.

To 12 500 MKN-45 cells in 100 ml RPMI 1640 medium, 10% FBS the given concentrations of the monoclonal antibodies against catalase and the given concentrations of the salen-manganese complex EUK-134 (chloro[[2,2'-[1,2-ethanediylbis[(nitrilo-κN)methylidyne]]bis[6-methoxyphenolato-κO]]]-manganese) (a catalase mimetic) were added and the incubation was continued for 2.5 hours at 37° C., 5% CO$_2$. Subsequently, the percentage of apoptotic cells (duplicates) was determined according to the conventional apoptosis criteria membrane blebbing, nuclear condensation and/or nuclear fragmentation.

Figure 9:
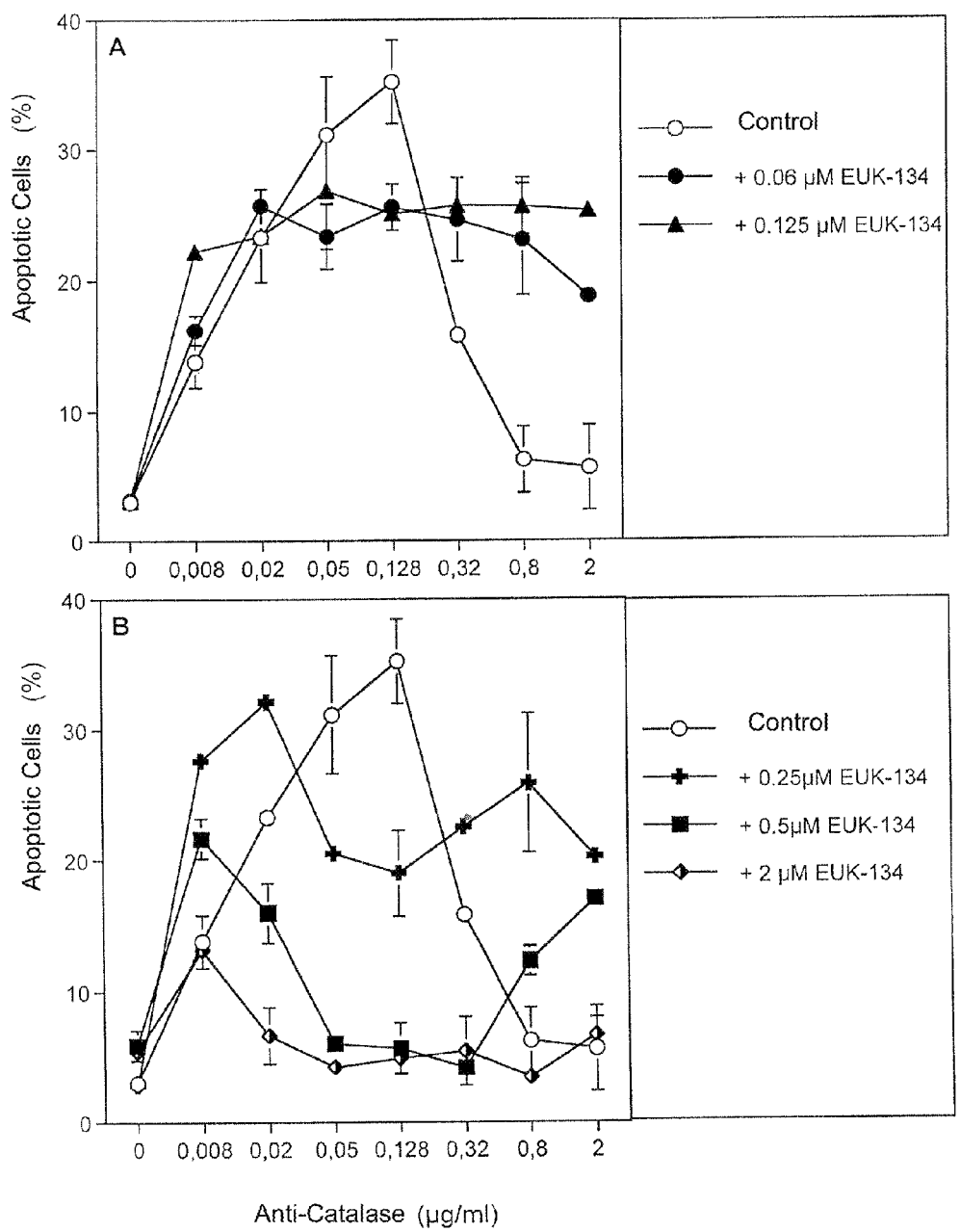
FIG. 9, parts A and B, explain the multifarious role of hydrogen peroxide in the intercellular ROS signaling.

FIG. 9 shows that very low concentrations of the catalase mimetic only have a minor influence on the signaling until the optimum range, but very clearly bring the supra-optimum range towards the optimum, since they decompose the excess hydrogen peroxide initiating the consumption reaction with HOCl. In the middle and higher concentration range of EUK-134 the NO/peroxynitrite pathway is at first favored and then in turn inhibited. Finally, the HOCl pathway is inhibited by the middle and higher concentrations of EUK-134.

FIG. 9 examines the cause for the occurrence of an optimum curve in the induction of apoptosis in tumor cells by monoclonal antibodies against catalase. Different concentrations of the salen manganese complex EUK-134 are employed in this analysis. EUK-134 acts as a catalase mimetic, but can also decompose peroxynitrite (Ophoven S and Bauer G. Salen manganese complexes: sophisticated tools for the analysis of intercellular ROS signaling pathways. Anticancer Res. 30: 3967-3980, 2010). However, for steric and kinetic reasons decomposing the peroxynitrite that is directly formed after catalase inhibition at the cell membrane of tumor cells requires relatively high concentrations of EUK-134. Thus, low concentrations of EUK-134 have essentially only an effect on hydrogen peroxide.

FIG. 9 shows that 0.06 and 0.125 mM EUK-134 change the optimum curve into a plateau curve. This shows that the supra-optimum drop of the induction of apoptosis is caused by excess hydrogen peroxide, of which is known from Bechtel W and Bauer G [(2009), Modulation of intercellular ROS signaling of human tumor cells, Anticancer Res. 29, 4559-4570; Heinzelmann S and Bauer G (2010), Multiple protective functions of catalase against intercellular apoptosis-inducing ROS signaling of human tumor cells, Biol. Chem. 391, 675-693] that it can consume HOCl and thus can lead to the termination of the HOCl pathway. Obviously, 0.06 and 0.125 mM EUK-134 compensate this consumption reaction, whereas they reduce the induction of apoptosis in the optimum to a much lower extent. 0.25 mM EUK-134 result in a significant increase in apoptosis in the lower concentration range of the antibodies, i.e. there where due to the data shown in FIG. 8 the NO/peroxynitrite signal pathway preferably runs. This stimulation of the NO/peroxynitrite pathway can be explained by the compensation of the consumption reaction between hydrogen peroxide and NO. In the middle concentration range of the antibody 0.25 µM EUK-134 as expected result in a stronger inhibition, since more hydrogen peroxide is removed from the system and thus the HOCl pathway is decelerated. In the high concentration range of the antibody the supra-optimum effect of excess hydrogen peroxide is further compensated and the reaction is brought to a plateau. The two next higher concentrations of EUK-134 then result in a complete inhibition of the HOCl pathway in the middle concentration range of the antibody and only enable the induction of apoptosis at very high antibody concentrations. At the same time, the stimulating effect of the EUK-134 on the NO/peroxynitrite pathway decreases again, since the decomposition of the formed peroxynitrite by EUK-134 now counteracts the increase in the signal pathway by the compensation of the consumption reaction between NO and hydrogen peroxide.

Example 2

Sensitization of Tumor Cells for Intercellular Induction of Apoptosis by the Effect of Monoclonal Antibodies Against SOD The published data suggest that catalase can effectively protect tumor cells from all intercellular ROS signal pathways and that accordingly an inhibition or inactivation of the catalase should be necessary and sufficient to compensate this protection again and to drive tumor cells into apoptosis by subsequently reactivated intercellular ROS signaling.

To 12 500 MKN-45 cells in 100 ml RPMI 1640 medium, 10% FBS the given concentrations of monoclonal antibodies against SOD and the given inhibitors were added and the incubation was continued for 6 hours at 37° C., 5% $CO_2$. Subsequently, the percentage of apoptotic cells (duplicates) was determined according to the conventional apoptosis criteria membrane blebbing, nuclear condensation, and/or nuclear fragmentation.

Inhibitors: 25 mM FeTPPS (peroxynitrite decomposition catalyst); 75 U/ml MnSOD; 50 mM taurine (HOCl scavenger); 2.4 mM L-NAME (NOS inhibitor).

The experiment shows that the monoclonal antibody against SOD in MKN-45 cells induces apoptosis that is exclusively based on the NO/peroxynitrite pathway. Under these conditions the HOCl pathway seems to play no role. The enhancing effect of taurine is based on the fact that the elimination of HOCl by taurine accelerates the reaction of hydrogen peroxide, so that the consumption reaction between hydrogen peroxide and NO is diminished and thus the NO/peroxynitrite pathway is enhanced.

Figure 10:
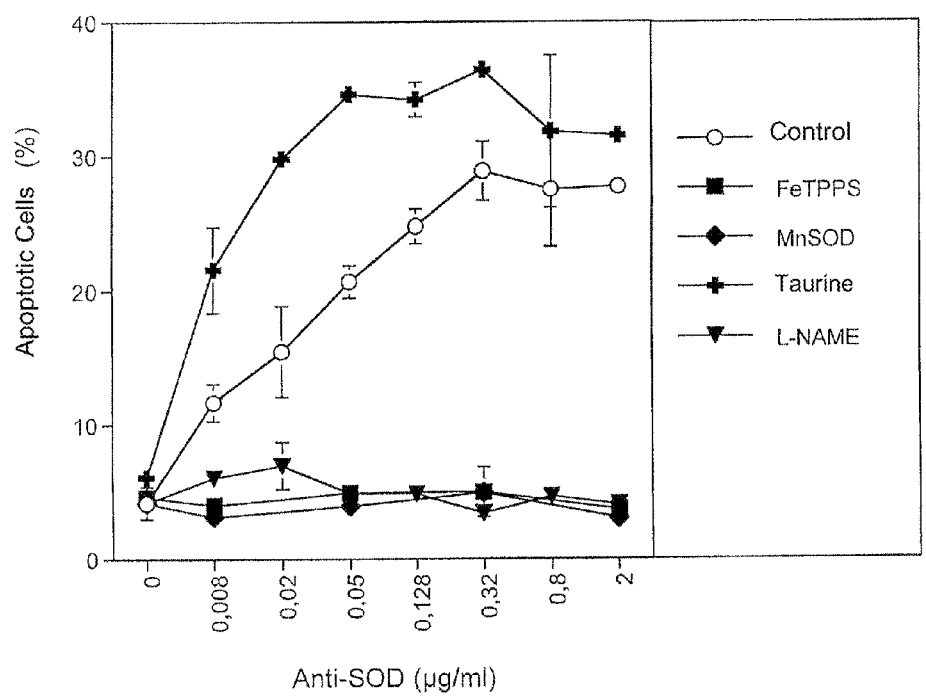
FIG. 10 shows the specific induction of apoptosis in MKN-45 cells by monoclonal antibodies against SOD.

Thus, the findings of the induction of apoptosis in tumor cells by monoclonal antibodies against SOD shown in FIG. 10 are unexpected and at first difficult to place at first sight. FIG. 10 shows that the addition of anti-SOD to the gastric carcinoma cell line MKN-45 results in a concentration dependent induction of apoptosis that depends on superoxide anions (inhibition by SOD), NO (inhibition by L-NAME), and peroxynitrite (inhibition by FeTPPS), i.e. the conventional players of the NO/peroxynitrite pathway, whereas the lacking inhabitability by taurine suggests that under these conditions the HOCl pathway plays no role. The enhancing effect of taurine on the NO/peroxynitrite pathway can be explained by the compensation of the consumption reaction between NO and hydrogen peroxide. In the presence of taurine with the here obviously marginally running HOCl synthesis by eliminating the HOCl the reaction of hydrogen peroxide by peroxidase is accelerated and thus the consumption reaction of NO is diminished. The increase in NO and its supply to the NO/peroxynitrite signal pathway apparently make a stronger impact than the loss of HOCl.

300 000 MKN-45 cells/ml were transfected with the given siRNAs (24 nM) and washed after 24 hours and taken up in fresh medium without siRNA. Antibodies against catalase or SOD were applied at the given concentrations. After 2.5 hours of incubation the percentages of apoptotic cells were determined in duplicates.

The experiment shows that siRNA against NOX-1, TGF-beta, and TGF-beta receptor inhibits the induction of apoptosis by anti-catalase and anti-SOD very strongly and over the entire concentration range. Induction of apoptosis by anti-catalase depends on iNOS and Duox-1, whereas the induction of apoptosis after administration of anti-SOD substantially depends on iNOS.

Figure 11:
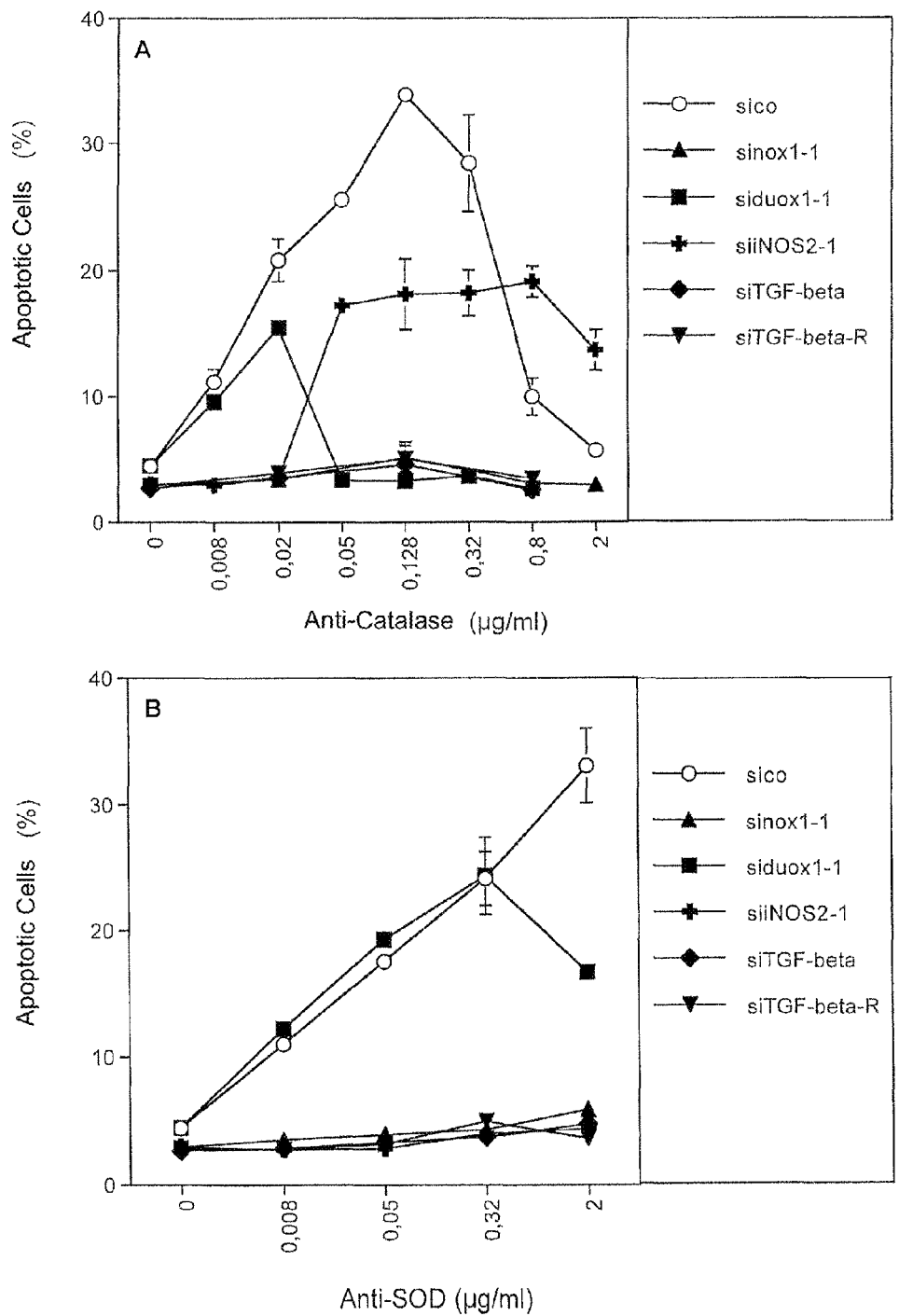
FIG. 11 summarizes experiments demonstrating an siRNA-supported analysis of the signal components for the induction of apoptosis by anti-catalase (FIG. 11A) and anti-SOD (FIG. 11B).

FIG. 11 shows that in the induction of apoptosis in MKN-45 tumor cells both by anti-catalase and anti-SOD the signal components NOX-1 as well as TGF-beta and TGF-beta receptor are of crucial importance. The induction of apoptosis by anti-catalase in the lower concentration range of the antibody above all is based on the effect of iNOS, whereas with higher concentrations iNOS and Duox-1 interact. However, the induction of apoptosis by anti-SOD is almost completely based on NOX-1 and iNOS, whereas also here TGF-beta and TGF-beta receptor are indispensable for the effect.

To 12 500 cells of the human neuroblastoma line SHEP and the human Ewing's sarcoma line SKN-MC in 100 ml EMEM plus 5% FBS the given concentrations of anti-catalase and anti-SOD, respectively, were added. The percentages of apoptotic cells were determined after 5 hours (SHEP) and 5.5 hours (SKNMC), respectively.

The result shows that the induction of apoptosis by antibodies against catalase or SOD is not only restricted to the cell line MKN-45, but broadly applicable.

Parallel controls with control IgG showed no induction of apoptosis (data not shown).

Figure 12:
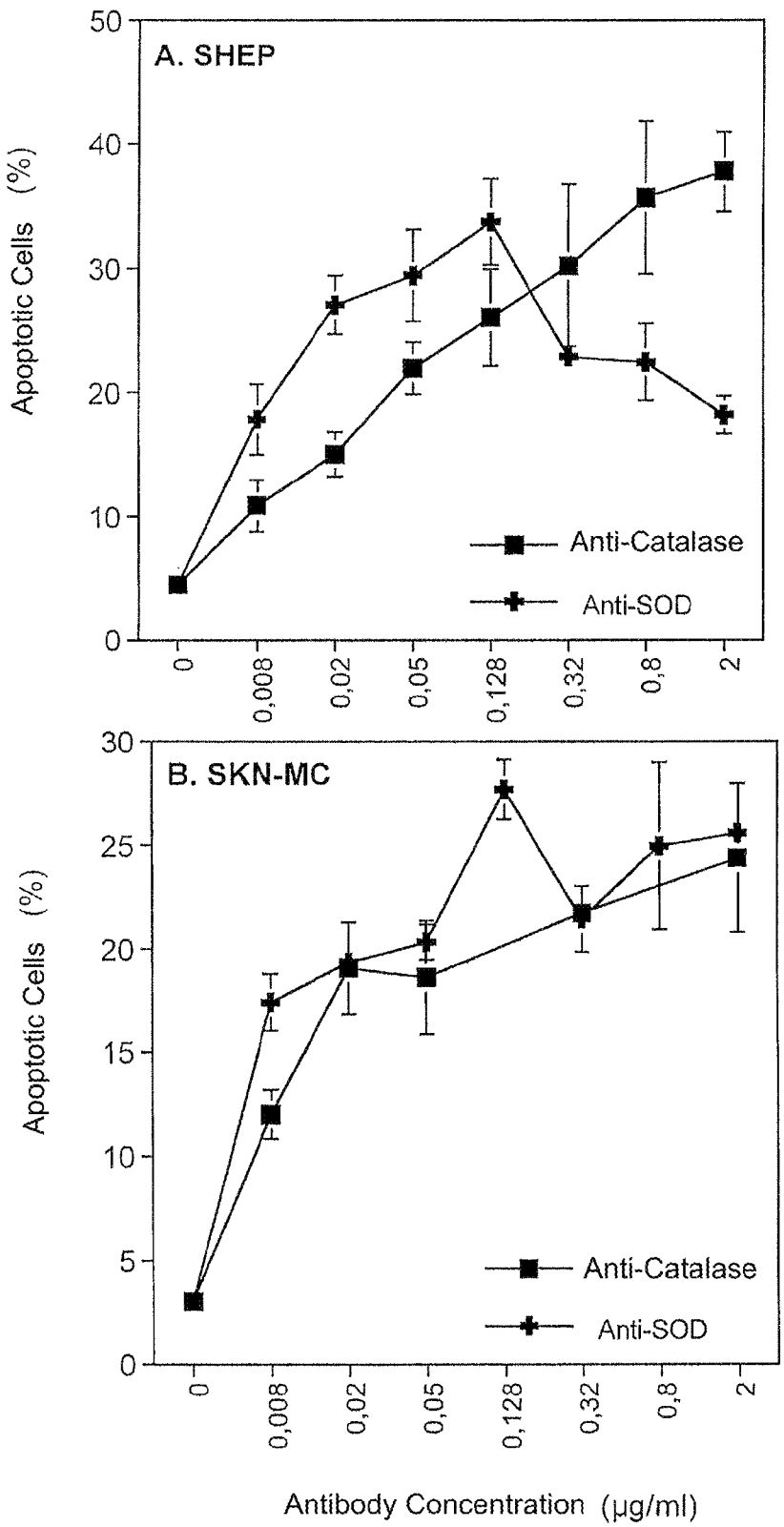
FIG. 12 shows that monoclonal antibodies against catalase and SOD induce apoptosis in the cell lines SHEP (FIG. 12A) and SKN-MC (FIG. 12B).

FIG. 12 shows the universal applicability of the new and unexpected findings, namely that both anti-catalase and anti-SOD are capable to induce apoptosis in tumor cells. With the help of the neuroblastoma line SHEP and the Ewing's sarcoma line SKNMC it is demonstrated that both anti-catalase and anti-SOD result in the induction of apoptosis that directly depends on the concentration of the respective antibodies.

To 10 000 cells of the human Ewing's sarcoma line SKN-MC in 100 ml EMEM plus 5% FBS the given inhibitors and the concentrations of anti-catalase and anti-SOD, respectively, plotted in the abscissa were added. The percentages of apoptotic cells were determined after 3 hours.

Inhibitors: 50 mM taurine (HOCl scavenger); 40 mM FeTPPS (peroxynitrite decomposition catalyst); 1000 U/ml catalase from ox liver; 40 mM MnTE2PyP(SOD mimetic); 90 U/ml MnSOD; 20 mM 3-Br-7-nitroindazole (nNOS specific inhibitor).

The figure shows that the Ewing's sarcoma line SKNMC both by anti-catalase and anti-SOD for the intercellular ROS signaling is exclusively sensitized via the NO/peroxynitrite pathway. The HOCl pathway seems to play no role, as can be seen from the lacking inhabitability by the HOCl scavenger taurine. Also noteworthy and important is the finding that the effect of anti-SOD can be compensated by exogenous catalase what indicates that anti-SOD could also result in an inhibition of tumor cell catalase.

Figure 13:
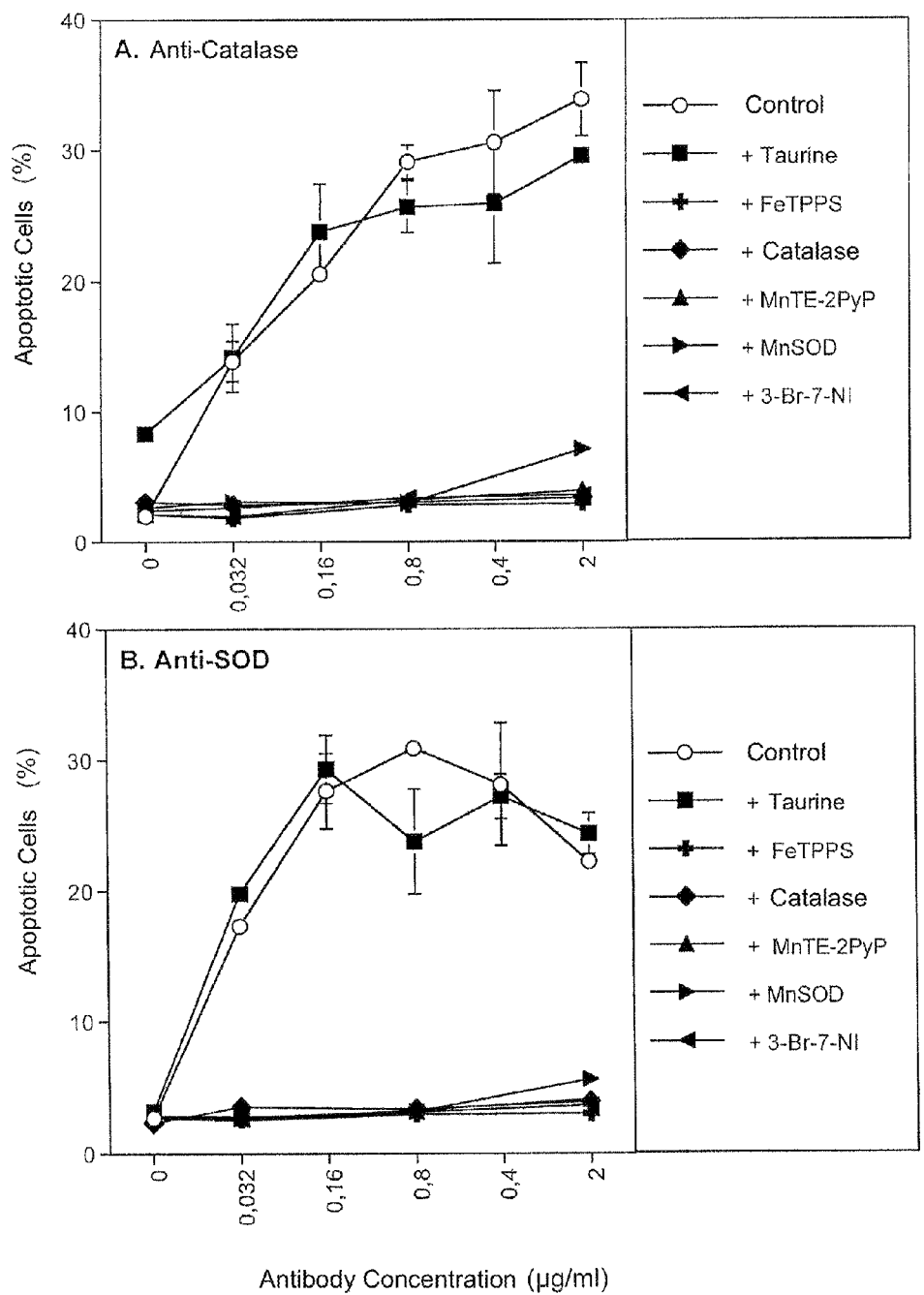
FIG. 13 shows that the induction of apoptosis in SKNMC cells by anti-catalase (FIG. 13A) and anti-SOD (FIG. 13B) is mediated by ROS signaling.

On the basis of the cell line SKN-MC FIG. 13 shows that both anti-catalase and anti-SOD sensitize the cells for intercellular ROS signaling with the help of the NO/peroxynitrite signal pathway, since a dependence on superoxide anions (inhibition by SOD and the SOD mimetic MnTE2PyP), NO (inhibition by the nNOS specific inhibitor 3-Br-7-nitro-indazole) and their reaction product peroxynitrite (inhibition by FeTPPS) is proved. Here, the HOCl pathway seems to play no recognizable role, as can be seen from the lacking inhibitory effect of taurine. The inhibition by the high concentration of catalase to be exogenously given is consistent with the assumption that high concentrations of exogenous catalase can detoxify peroxynitrite formed at the cell membrane by the cells themselves before it induces apoptosis by lipid peroxidation. The same function can be performed by membranous catalase of the tumor cells. The finding that in said cell system exclusively performing signaling via the NO/peroxynitrite pathway the effect of anti-catalase can be compensated again by exogenous catalase is conclusive and to be demanded as a control. However, that the effect of anti-SOD (in which theoretically no influence on the sufficiently protecting catalase zone on the outer membrane of the cells is to be expected) is also compensated by high catalase concentrations now for the first time refers to the fact that the inhibition of the SOD must also have a negative influence on the protective catalase of the tumor cells.

To 4000 MKN-45 cells in 100 ml RPMI 1640 medium, 10% FBS the given concentrations of anti-catalase and anti-SOD, respectively, and as a control anti-EGF receptor were added. After 15 minutes, either 200 mM peroxynitrite (PON), 0.5 mM of the NO donor DEA-NONOate, or 2 mU/ml glucose oxidase (hydrogen peroxide generator) were added. After 2 hours of incubation at 37° C., 5% $CO_2$ the percentages of apoptotic cells were determined in duplicates.

This figure impressively shows that both anti-catalase and anti-SOD, but not the irrelevant control antibody, result in an inhibition of the catalase activity of the tumor cells, since now these become sensitive to the catalase substrates peroxynitrite (either directly added or formed by the interaction of NO from the NO donor and superoxide anions generated by cells) and hydrogen peroxide. The optimum curve with the peroxynitrite effect can be explained by the fact that with an increase in the catalase inhibition a cell's own hydrogen peroxide results in a consumption of peroxynitrite.

Figure 14:
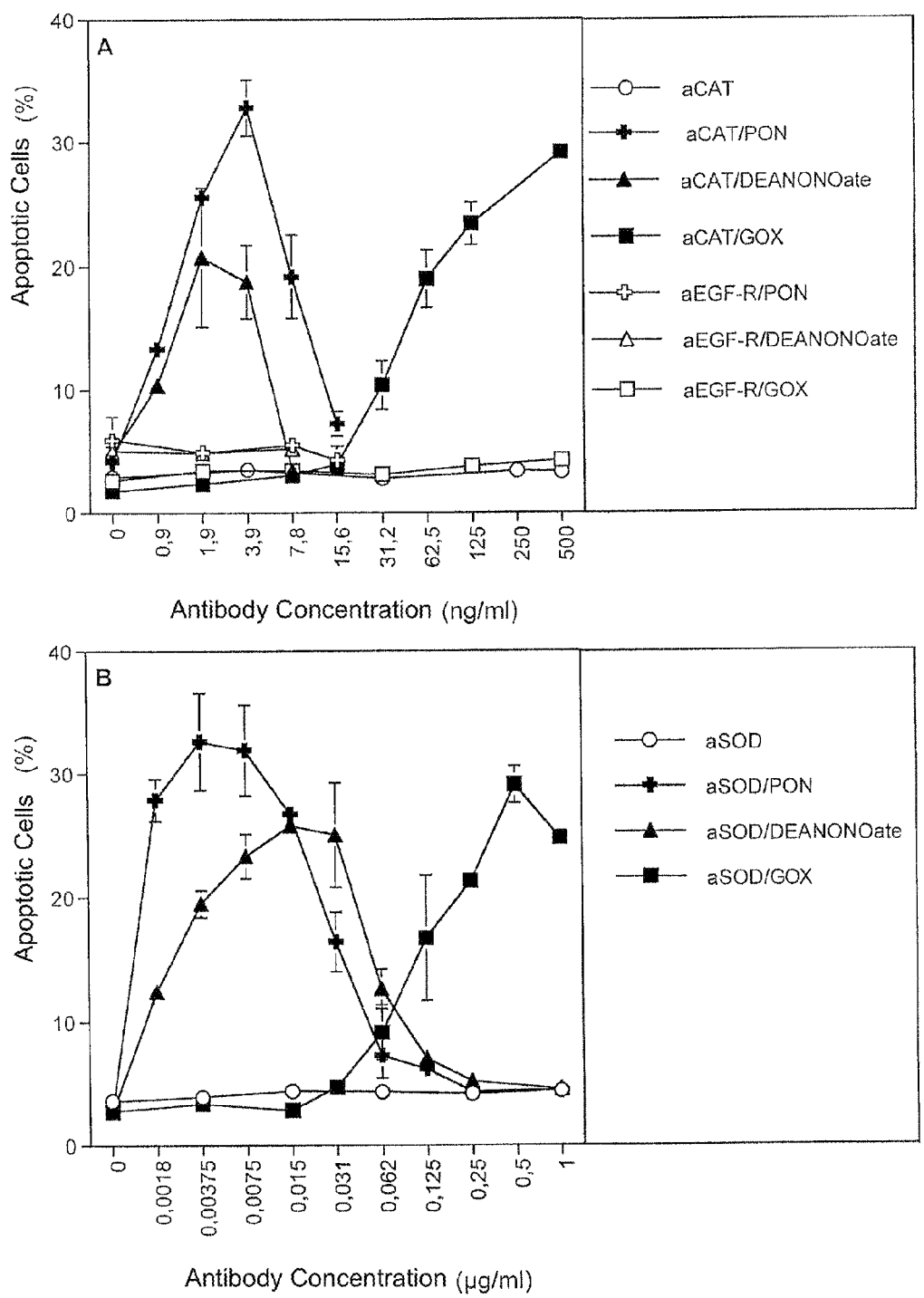
FIG. 14 shows that anti-catalase (FIG. 14A) and anti-SOD (FIG. 14B) antibodies result in an inhibition of the tumor cell catalase.

It is shown in FIG. 14 that the addition of antibodies both against catalase and against SOD results in a sensitization of MKN-45 tumor cells against the apoptosis-inducing effect of peroxynitrite and hydrogen peroxide. In this experiment peroxynitrite both is directly added and formed after the application of the NO donor DEA-NONOate on the cell membrane by the interaction of NO released from the NO donor with superoxide anions formed by NOX-1. Directly apoptosis-inducing hydrogen peroxide concentrations are generated by glucose oxidase. FIG. 14 shows that both anti-catalase and anti-SOD sensitize the cells against peroxynitrite and hydrogen peroxide. Sensitization against peroxynitrite occurs in the lower concentration range of the antibodies and has the form of an optimum curve. As shown in Heinzelmann and Bauer 2010 the declining part of the optimum curve is dependent on the consumption of peroxynitrite by hydrogen peroxide. Sensitization against exogenously generated hydrogen peroxide requires higher concentrations of the antibodies. Control antibodies directed against the membranous EGF receptor had no sensitizing effect. The findings shown in FIG. 14 pose a challenge to the interpretation skills of the experimenter. Assuming that tumor cells are protected from the intercellular signaling by catalase alone the sensitization of the cells to NO, peroxynitrite, and hydrogen peroxide by anti-catalase is expected, however sensitization by anti-SOD is unexpected. Assuming that the cells carry both catalase and SOD on their membrane for the protection of the cells from ROS there is an excellent cooperation opportunity and mutual potentiation of both enzymes, as is illustrated in FIG. 2. Accordingly, catalase would prevent the HOCl synthesis by decomposing hydrogen peroxide and interrupt the NO/peroxynitrite pathway by degrading peroxynitrite. SOD would prevent the formation of peroxynitrite and additionally prevent the interaction of HOCl and superoxide anions. That is, each of the two signal pathways would be inhibited at two different locations by the interaction of SOD and catalase.

Figure 3:
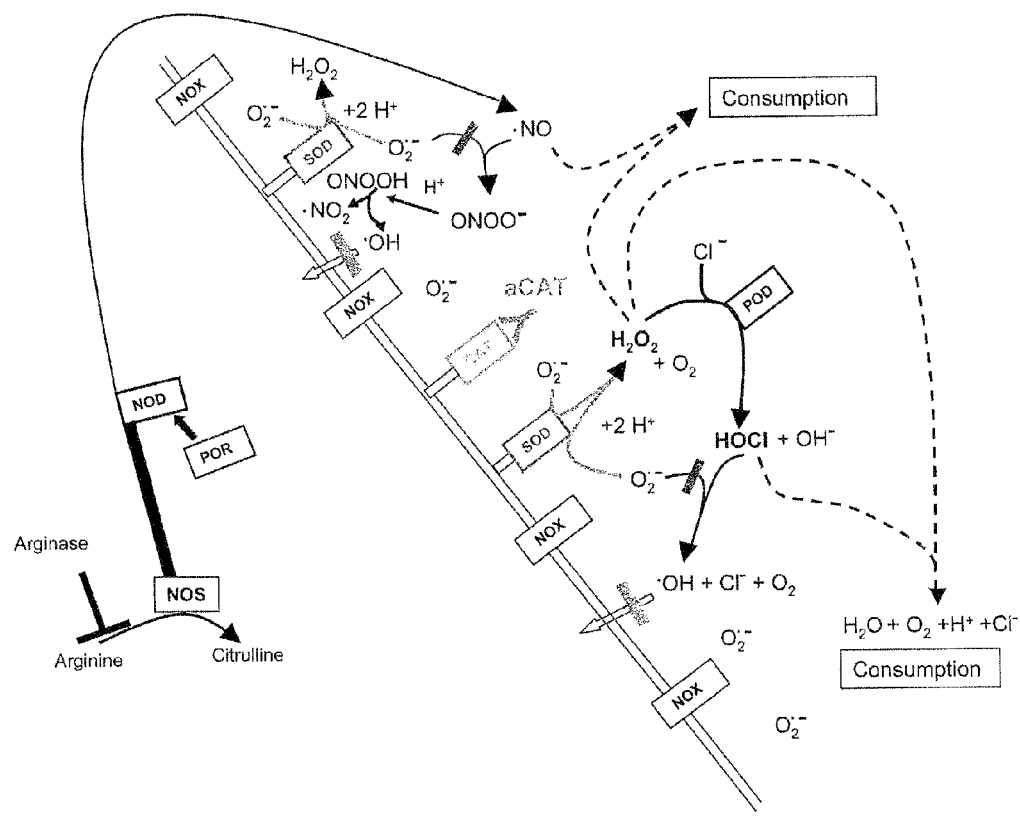
FIG. 3 depicts a theoretical reaction scheme concerning the inhibition of catalase, more particularly demonstrating how the specific inhibition of the catalase by monoclonal antibodies (aCAT) should not be sufficient to reactivate the signaling, since each of the two signal pathways should also be inhibited by SOD at a central location. However, the findings experimentally collected contradict this simple view.
Figure 4:
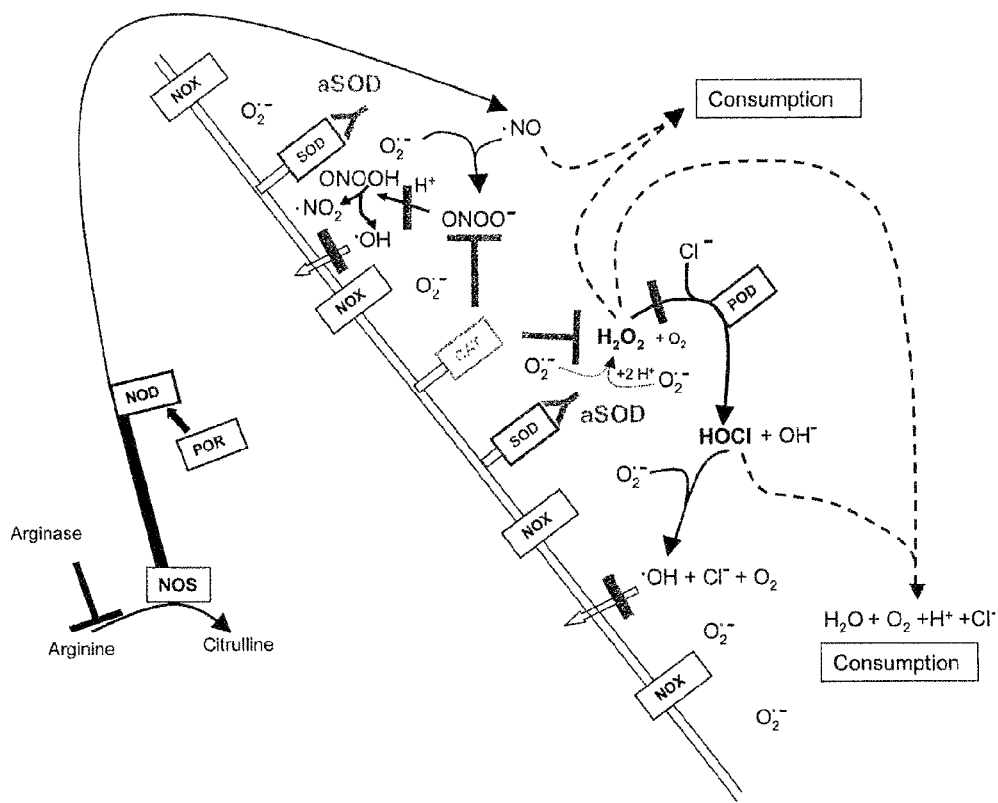
FIG. 4 depicts a theoretical reaction scheme concerning the inhibition of the SOD, more particularly demonstrating the complementary procedure, namely the exclusive specific inhibition of the SOD by antibodies (aSOD) also should not result in a reactivation of the signaling, since the catalase can block both signal pathways by degrading peroxynitrite and hydrogen peroxide.
Figure 5:
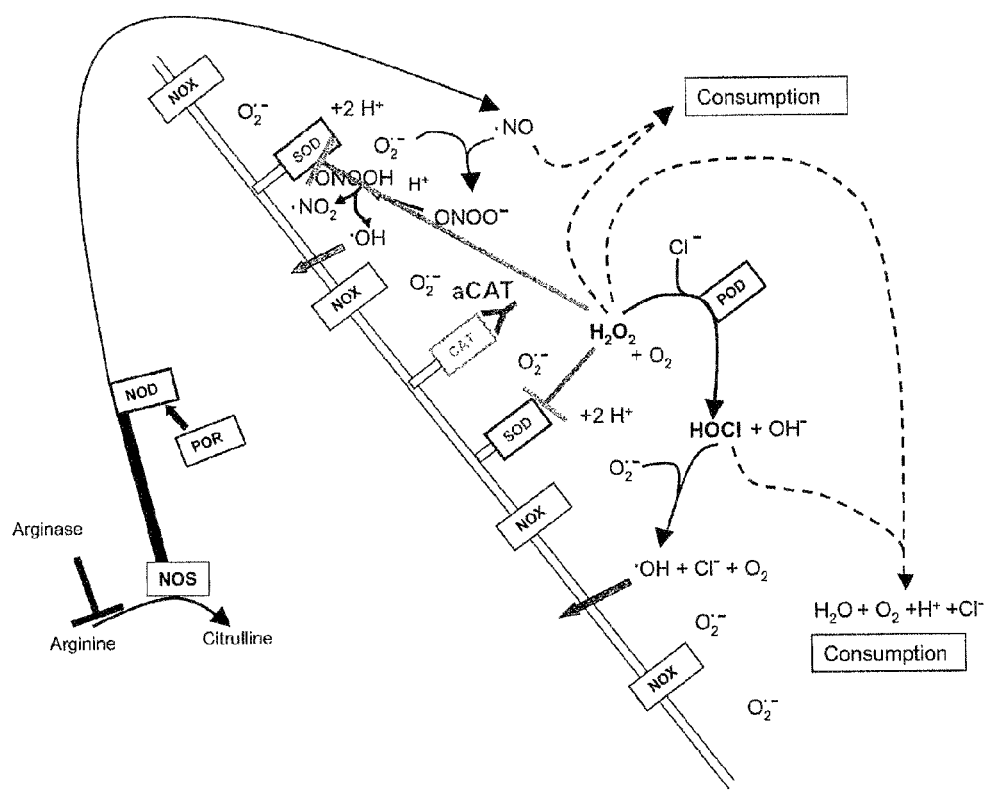
FIG. 5 depicts a theoretical reaction scheme demonstrating how the inhibition of catalase by the hydrogen peroxide that is now locally present in a relatively high concentration (from a spontaneous and SOD catalyzed dismutation reaction) results in an inhibition of SOD and thus the course of both signal pathways all in all is possible.
Figure 6:
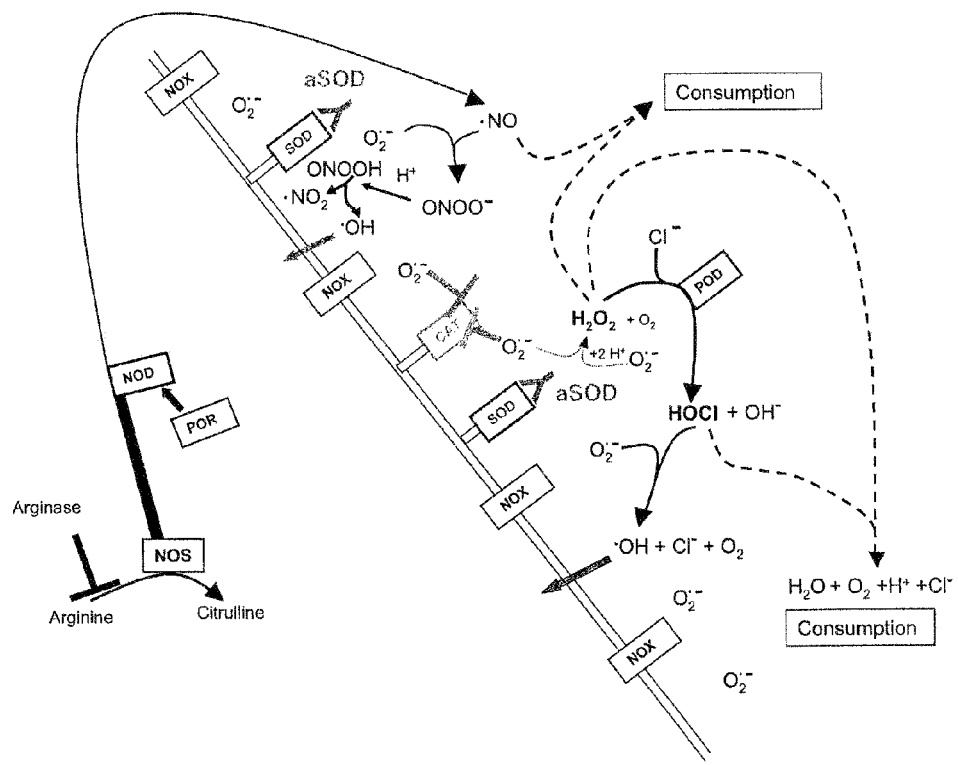
FIG. 6 depicts a theoretical reaction scheme demonstrating how the inhibition of SOD results subsequently in the inhibition of catalase. More particularly, the schematic drawing shows that after inhibition of SOD superoxide anions that are present in a high local concentration result in an inhibition of catalase and thus the multiple inhibition of both signal pathways is canceled.

Considering the result represented in FIG. 14 from the standpoint of FIGS. 2 and 3 so the sensitization of the cells to exogenously added peroxynitrite and hydrogen peroxide by anti-catalase is further conclusive, however, not the sensitization to peroxynitrite formed of NO and cell's own superoxide anions, since here, according to the biochemical context represented in the schematic drawing, SOD should further prevent the formation of peroxynitrite by eliminating the superoxide anions. In fact, the inhibition of the SOD by anti-SOD should allow the formation of peroxynitrite from NO and superoxide anions (see, FIG. 4), but then the not inhibited catalase should degrade the peroxynitrite. From a simple inhibition of the SOD it can also not be explained on which way the cell is sensitized against exogenous peroxynitrite and hydrogen peroxide by anti-SOD. The results shown in FIG. 14 can immediately be explained conclusively in all points if it is assumed that the administration of anti-catalase antibodies also results in an inactivation of SOD and the administration of anti-SOD antibodies also results in an inactivation of the catalase. Due to the monoclonal nature of the two antibody preparations and the specificity testing by the manufacturer neither cross contamination nor cross-reaction are suitable to explain these findings. The following FIGS. 15 and 16 solve this important question.

At first, 4000 MKN-45 cells in 100 ml RPMI 1640 medium, 10% FBS remained untreated or received 5 mM or 100 mM AEBSF (inhibitor of the NADPH oxidase). Subsequently, either no antibodies ("control"), 10 ng/ml anti-SOD ("aSOD"), 5 ng/ml anti-catalase ("aCAT"), or a combination of anti-SOD and anti-catalase ("aSODS+aCAT") are added. After additional 15 minutes 100 mM peroxynitrite (PON) (A) are added. Control batches (B) remained free of peroxynitrite. The percentages of apoptotic cells were determined in duplicates after 2 hours.

Figure 15:
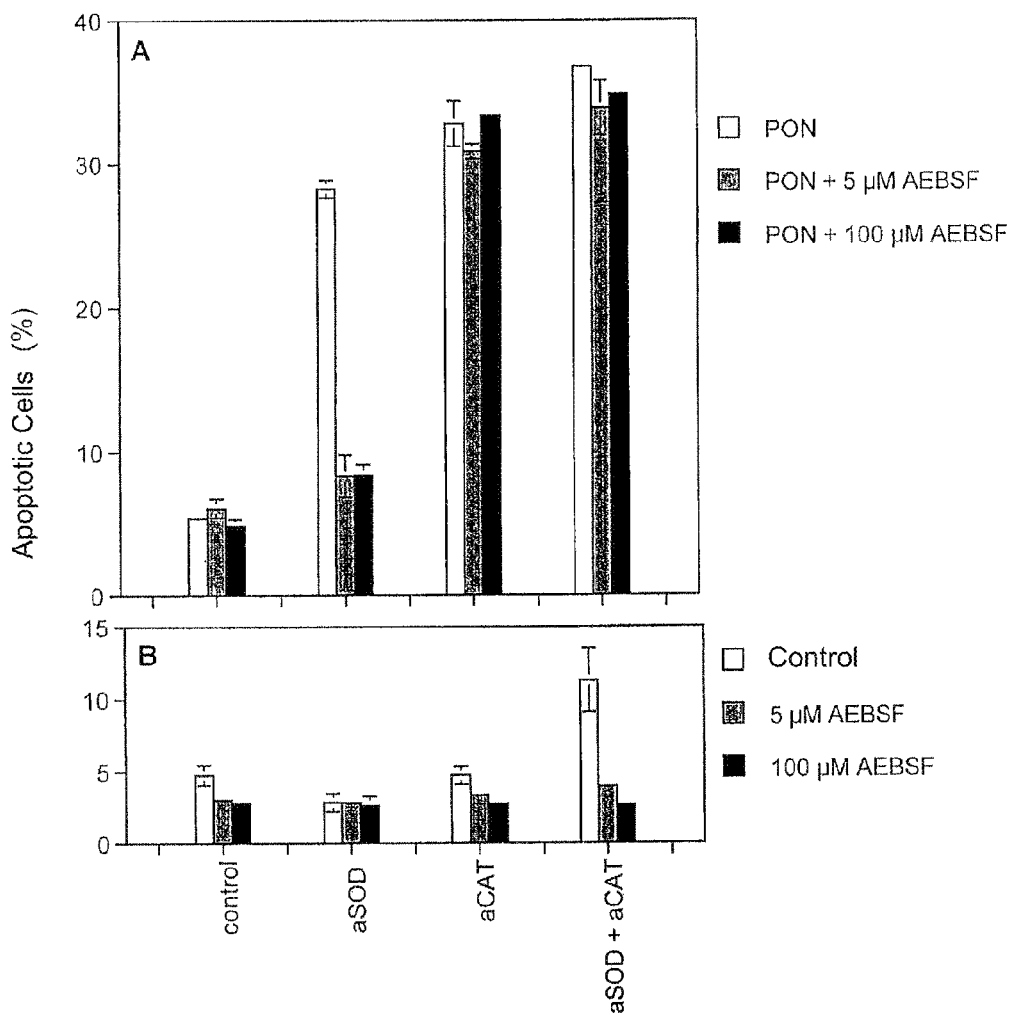
FIG. 15, parts A and B, demonstrates the importance of superoxide anions for the sensitization of tumor cells against exogenous peroxynitrite by anti-SOD and anti-catalase.

FIG. 15 shows that the catalase inhibition of the tumor cells by anti-catalase even runs successfully if the NADPH oxidase is partially or completely inhibited. However, the effect of anti-SOD on the tumor cell catalase that is expressed in the sensitization to peroxynitrite depends on an optimally running production of superoxide anions. First, this shows that anti-SOD does not posses a direct inhibitory effect for catalase, otherwise its effect with respect to lacking inhabitability by AEBSF should be equal to that of anti-catalase. The result also shows that anti-SOD has an indirect effect on the tumor cell catalase-mediated by superoxide anions (or their subsequent product).

FIG. 15 shows that both anti-catalase antibodies and anti-SOD antibodies sensitize MKN-45 cells to the effect of exogenously added peroxynitrite. If the respective administration of the antibodies is done after the cells have been treated with AEBSF, an inhibitor of the NADPH oxidase, so as expected anti-catalase further has a sensitizing effect. However, the effect of anti-SOD antibodies on the sensitization against peroxynitrite, a process that can only be explained by a simultaneous compensation of the catalase activity of the tumor cells, completely fails to come in the presence of AEBSF. That means that the effect of aSOD requires the synthesis of superoxide anions or the effect of their subsequent products.

First, 4000 MKN-45 cells in 100 ml RPMI 1640 medium, 10% FBS remained untreated or received 5 mM or 100 mM AEBSF (inhibitor of the NADPH oxidase). Subsequently, either no antibodies ("control"), 10 ng/ml anti-SOD ("aSOD"), 5 ng/ml anti-catalase ("aCAT"), or a combination of anti-SOD and anti-catalase ("aSOD+aCAT") were added. After additional 15 minutes 0.5 mM DEA-NONOate, a rapidly decomposing NO donor (A), were added. Control batches remained free of DEA-NONOate (B). The percentages of apoptotic cells were determined in duplicates after 2 hours.

It is important for the understanding of this result that at first it must be recapitulated that after the release of NO from DEA-NONOate it reacts with superoxide anions of the cell to peroxynitrite which then induces apoptosis. Thus, this process can be blocked both by SOD and catalase. Since it can be seen from the data shown so far that the tumor cells carry both catalase and SOD on their surfaces the finding that both anti-SOD and anti-catalase result in a sensitization to the DEA-NONOate effect leads to the conclusion that the treatment with anti-SOD also inactivates the catalase and the treatment with anti-catalase also inactivates SOD. In the presence of 5 mM AEBSF this correlation seems not to work any more, since under these conditions the effect of the administration of anti-SOD or anti-catalase alone, but not the effect of the combination of both antibodies is prevented. The functioning of the combination of the antibodies in the presence of 5 mM AEBSF shows that here still sufficient superoxide anions are available for the formation of peroxynitrite, whereas this certainly is not the case any more with 100 µM AEBSF. All together, the finding can be explained best by the fact that anti-SOD in a superoxide anions-dependent process also inhibits catalase, conversely anti-catalase in a superoxide anions-dependent process inhibits SOD, so that the administration of one of these two antibodies is sufficient to run the entire process. In the presence of 5 mM AEBSF the mutual inhibition fails to come, thus now both antibodies must be present to achieve a sensitization.

Figure 16:
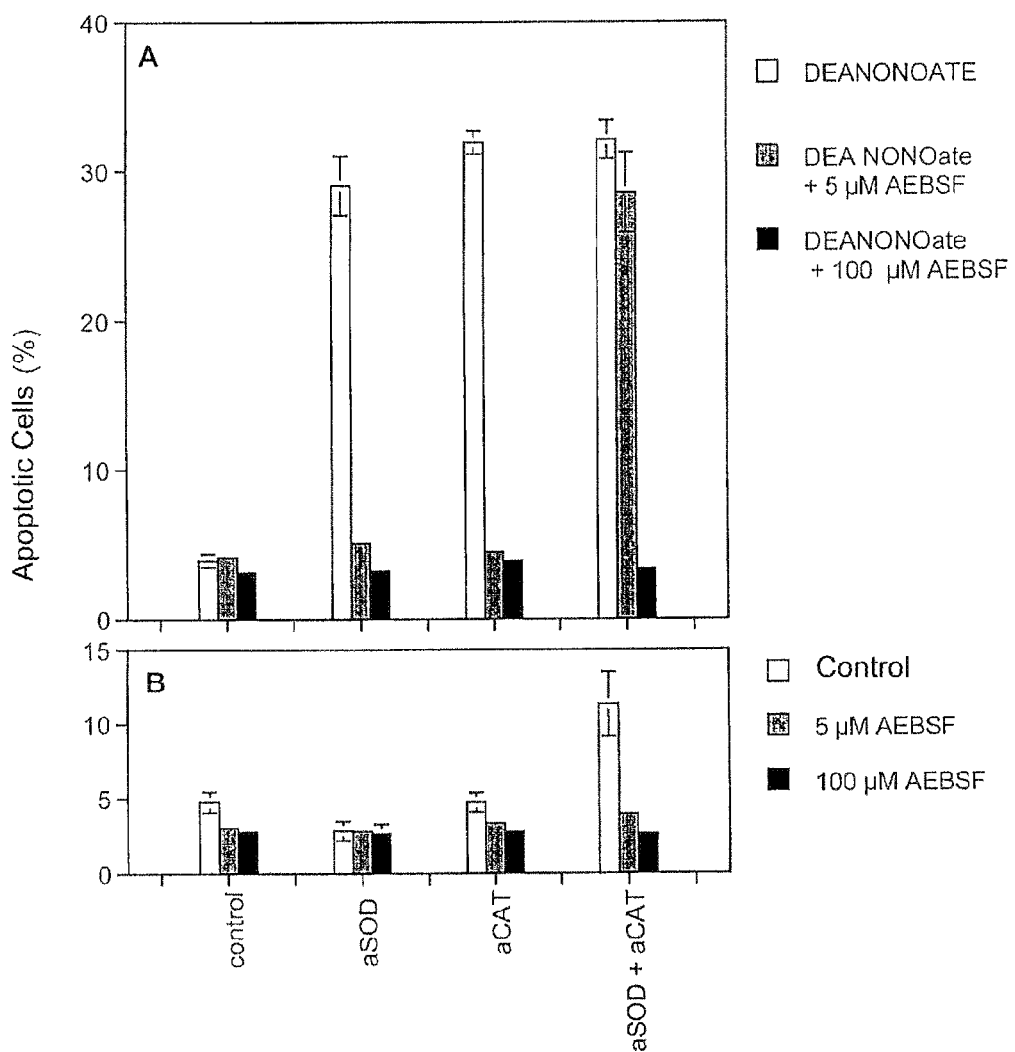
FIG. 16, parts A and B, demonstrates the importance of superoxide anions for the anti-catalase and anti-SOD-dependent sensitization of tumor cells against peroxynitrite formed by the interaction of an exogenous NO donor with extracellular superoxide anions of the tumor cell against exogenous peroxynitrite by anti-SOD and anti-catalase.

FIG. 16 broadens the understanding of the correlation between anti-SOD and anti-catalase. In this experiment the formation of the apoptosis inductor peroxynitrite is enabled by the administration of the exogenous NO donor DEA-NONOate and the availability of cellular superoxide anions. Also here, the application of either anti-catalase or anti-SOD alone results in a sensitization of the cells to the induction of apoptosis. Both the partial inhibition of the production of superoxide anions by 5 mM AEBSF and its complete inhibition by 100 mM AEBSF prevents the apoptosis-inducing effect of anti-catalase antibodies and anti-SOD antibodies. In the presence of 100 mM AEBSF with the simultaneous administration of both antibodies there is no induction of apoptosis what is to be demanded by the absence of the formation of peroxynitrite with the completely prevented synthesis of superoxide anions. However, in the presence of 5 mM AEBSF the induction of apoptosis is not significantly inhibited by the simultaneous application of both antibodies, whereas the sensitizing effect of the administration of anti-catalase or anti-SOD alone in the presence of 5 mM AEBSF is completely compensated. This shows that in the presence of 5 mM AEBSF there are still sufficient superoxide anions present for the formation of peroxynitrite, because otherwise with the simultaneous administration of anti-SOD and anti-catalase the observed induction of apoptosis could not occur. The result also shows that the induction of apoptosis by peroxynitrite that is formed in the batch after the interaction of NO and superoxide anions is inhibited both by SOD and catalase, as is accordingly expected from FIG. 2. Thus, it can also be concluded that the administration of anti-SOD antibodies also leads to an inhibition of the catalase and that the administration of anti-catalase antibodies also leads to an inhibition of SOD and that these additional inhibitions of the other target require the presence of superoxide anions or their products. It is obvious to assume that the superoxide anions that are locally present in a high concentration in the inhibition of the catalase result in an inhibition of the catalase and the hydrogen peroxide occurring in the inhibition of the catalase in a high local concentration results in a substrate inhibition of the SOD.

Example 3

Synergistic Effect Between Anti-Catalase and Anti-SOD 12 500 MKN-45 cells in 100 ml RPMI 1640 medium, 10% FBS received the given concentrations of anti-catalase. Control batches remained free of additional batches, batches for determination of the interaction additionally received 0.5 ng/ml or 2 ng/ml anti-SOD. The percentages of apoptotic cells were determined after 5.5 hours in duplicates.

The result shows a very pronounced synergistic effect in the interaction of anti-SOD and anti-catalase.

Figure 17:
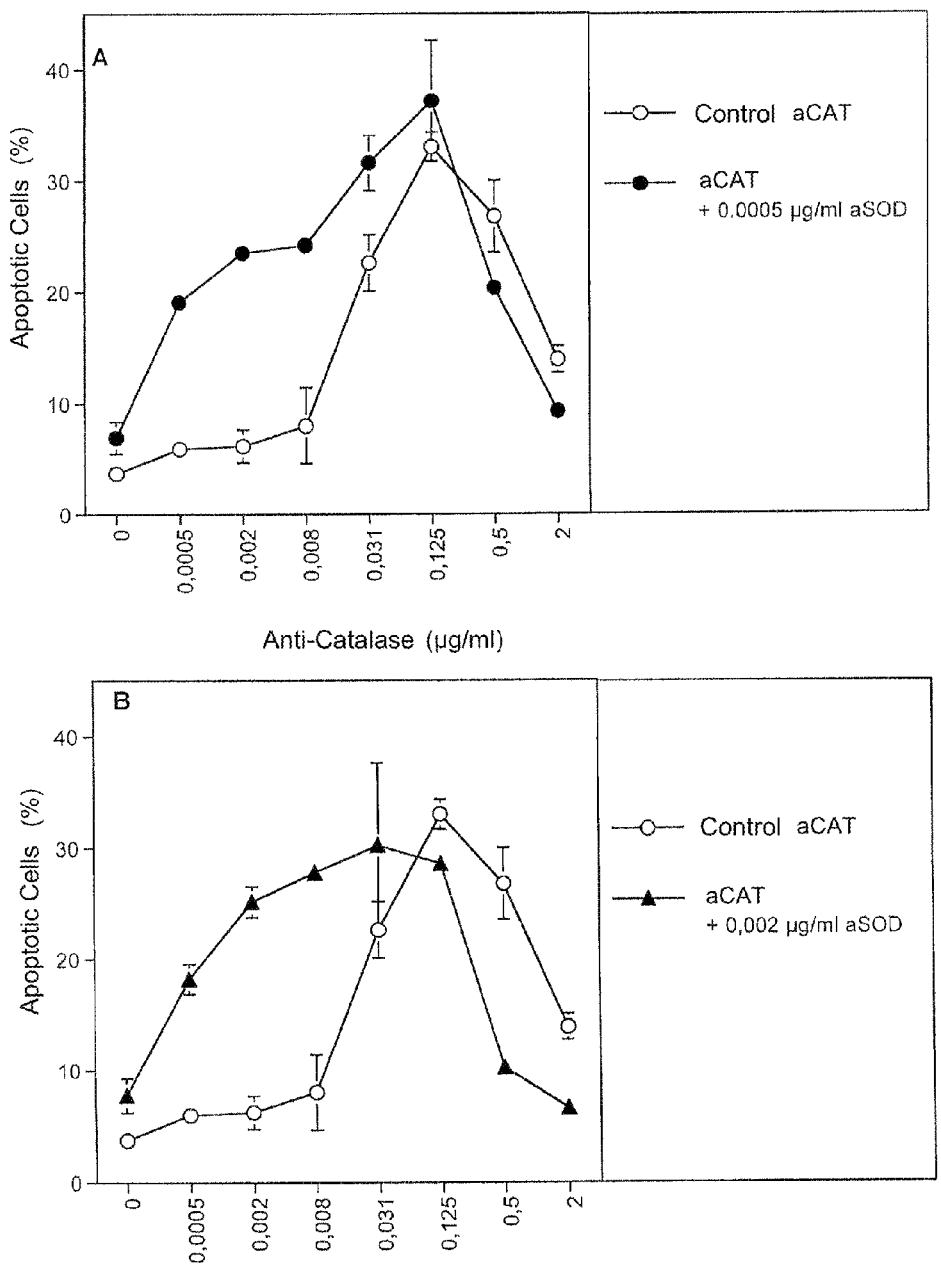
FIG. 17, parts A and B, shows a synergistic effect of antibodies against SOD and catalase in the ROS-mediated induction of apoptosis in tumor cells.

At first, FIG. 17 shows the effect of antibodies against catalase resulting in a concentration-dependent induction of apoptosis in the form of an optimum curve. The simultaneous addition of very low concentrations of aSOD, which by themselves cause a hardly recognizable induction of apoptosis, results in a very pronounced synergistic effect. This is unexpected and of great interest, since on its basis a considerable saving of antibodies could be achieved with the same effect. So, for example the combination of 2 ng/ml anti-SOD with 2 ng/ml anti-catalase results in 80 percent of the effect that can be achieved with 125 ng/ml of anti-catalase antibodies alone. 12 500 MKN-45 cells in 100 ml RPMI 1640 medium, 10% FBS received the given concentrations of anti-catalase (control), anti-catalase plus 2 mM histidine (singlet oxygen scavenger), anti-catalase plus 1 ng/ml anti-SOD, anti-catalase/1 ng/ml anti-SOD/2 mM histidine. The percentages of apoptotic cells are determined after 3 hours in duplicates.

The figure shows that the synergistic effect between anti-SOD and anti-catalase is not caused by singlet oxygen. However, the respective supra-optimum inhibition is compensated by histidine indicating a role of singlet oxygen in this concentration range.

Figure 18:
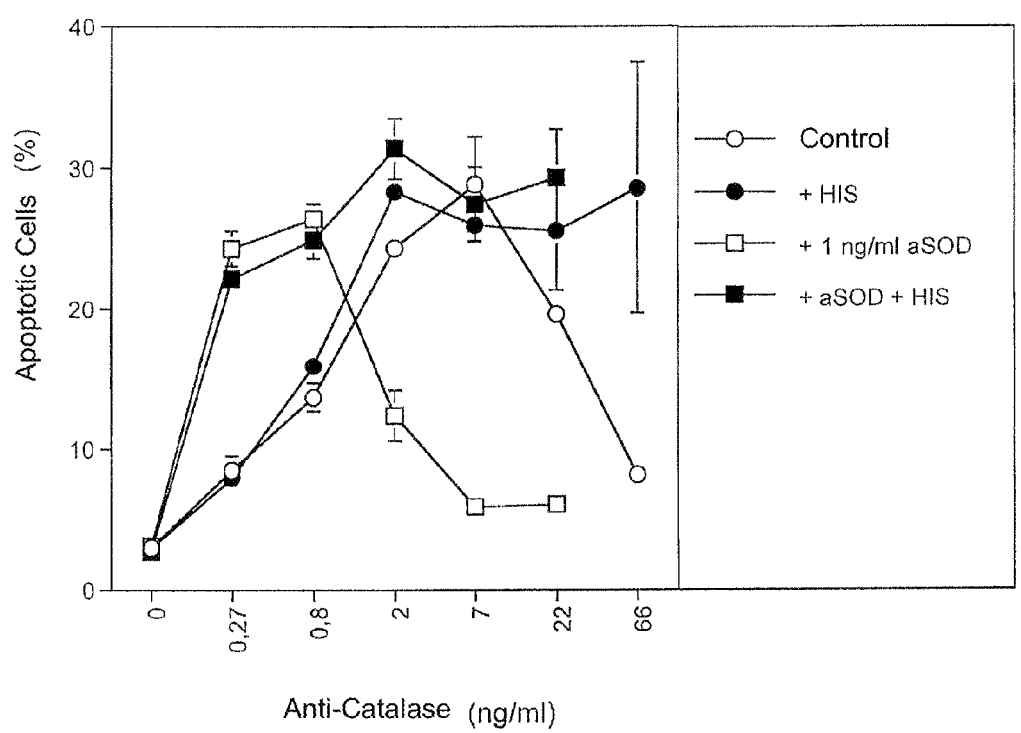
FIG. 18 shows that the synergistic effect between anti-SOD and anti-catalase is not mediated by singlet oxygen.

FIG. 18 shows that the synergistic effect between anti-SOD and anti-catalase is not based on a singlet oxygen effect, since the effect cannot be blocked by the singlet oxygen scavenger histidine. In this experiment there is demonstrated the important finding that the supra-optimum drop of the concentration-dependent curves each can be blocked by histidine. Due to the known signal pathways this can be explained by the fact that in the supra-optimum concentration range of the antibodies there is an inactivation of catalase due to the formation of singlet oxygen, which is why then the available concentration of peroxidase is no longer sufficient to convert all of the hydrogen peroxide into HOCl. In this way, the consumption reaction between HOCl and hydrogen peroxide represented in FIG. 9 and analyzed in more detail by Bechtel and Bauer, 2009, terminates the HOCl pathway.

12 500 MKN-45 cells in 100 ml RPMI 1640 medium, 10% FBS in experimental part A received the given concentrations of anti-catalase (monoclonal), humanized Fab fragments against catalase (AbD 15563, AbD 15562), in experimental part B the given concentrations of anti-SOD (monoclonal), humanized Fab fragments against SOD (AbD 15660, AbD 15661, AbD 15662). The duplicates in experimental part A were evaluated after 6 hours, that in experimental part B after 3 hours.

Figure 19:
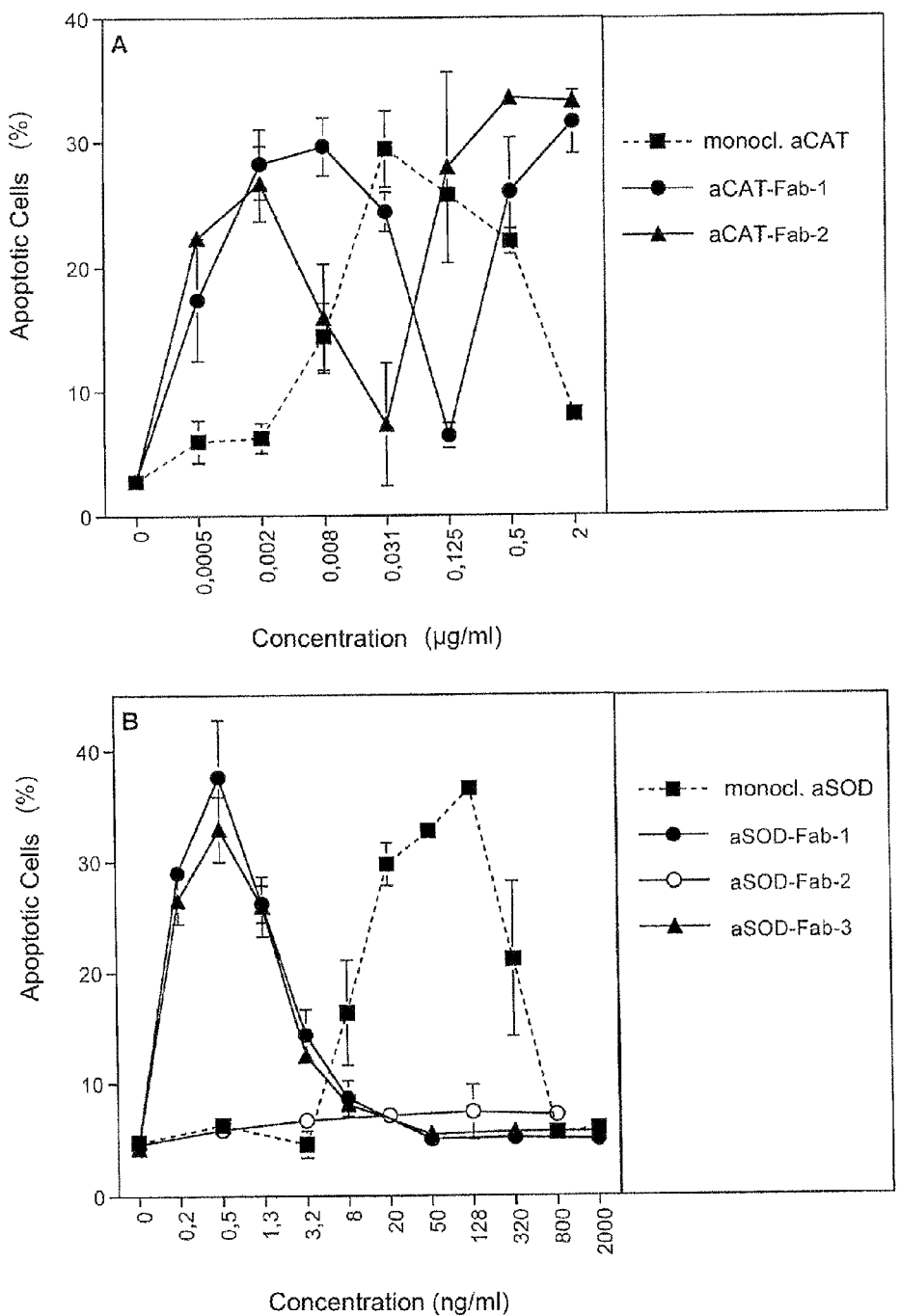
FIG. 19 explains the sensitization of the human tumor cell line MKN-45 by humanized Fab fragments against catalase (FIG. 19A) or SOD (FIG. 19B), respectively.

FIG. 19 shows that the humanized Fab fragments against catalase or SOD as well as monoclonal antibodies against the same target structures have a strong sensitizing effect on human tumor cells. This indicates that the specific binding of the antibodies or the Fab fragments, respectively, and the resulting inhibition are important for the observed induction of apoptosis. FIG. 19 also shows that it can be distinguished between Fab fragments binding to the target structure and such that also inhibit its function. So, all three represented Fab fragments against SOD bind to said enzyme, whereas only Fab-1 (AbD 15660) and Fab-3 (AbD 15662) also inactivate it and thus initiate ROS signaling.

FIG. 19 shows that the effect of the monoclonal antibody against catalase can also be achieved with the help of humanized Fab fragments. With the chosen application of the concentrations in mg/ml there is observed an expectedly greater effect of the Fab fragments. The concentration dependence of the effect of the Fab fragments is demonstrated as optimum curve. In parallel performed inhibitor experiments it is shown that in the area of the optimum curve this initially is the NO/peroxynitrite pathway that is then replaced by the HOCl pathway before this is inhibited by the previously discussed consumption reaction due to excessive hydrogen peroxide concentrations. The further addition of Fab against catalase in the range from 0.5 mg/ml results in the direct induction of apoptosis by hydrogen peroxide.

12 500 MKN-45 cells in 100 ml RPMI 1640 medium, 10% FBS received the given concentrations of the Fab fragment AbD15562 directed against catalase. Control batches remained free of further batches, batches for the determination of the interaction additionally received 0.002 ng/ml or 0.0078 ng/ml of the anti-SOD Fab fragment AbD 15660. The percentages of apoptotic cells were determined after 3 hours in duplicates.

This result shows that also with Fab fragments directed against catalase or SOD, respectively, a noteworthy synergistic effect in the induction of apoptosis in tumor cells can be achieved. The impressive low concentrations of Fab fragments needed for that encourage the hope to therefrom develop a financeable therapeutic approach.

Figure 20:
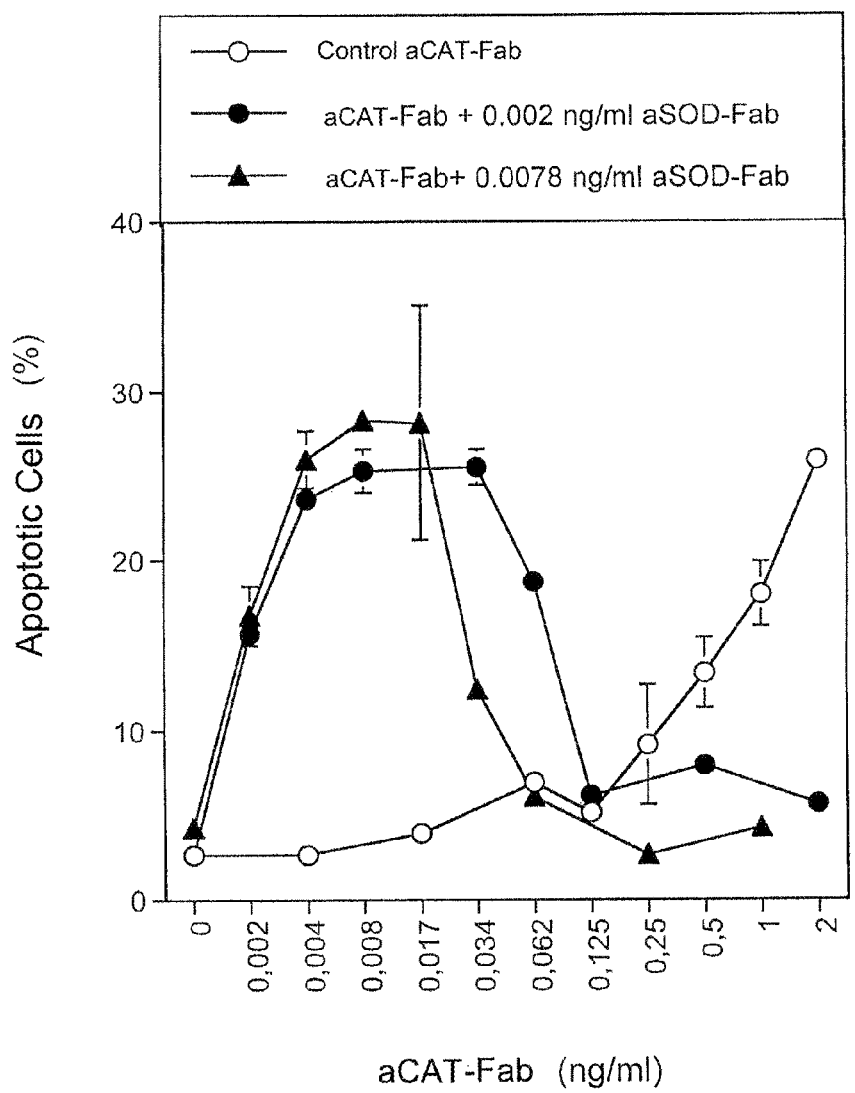
FIG. 20 shows the synergistic effect of Fab fragments against SOD and catalase in the ROS-mediated induction of apoptosis in tumor cells.

FIG. 20 shows that also Fab fragments humanized against SOD can be prepared that very efficiently induce apoptosis in human tumor cells. Also here, the expected higher efficacy in comparison to monoclonal antibodies is observed.

Finally, FIG. 20 shows that the combination of humanized Fab fragments against catalase with humanized Fab fragments against SOD results in a considerable synergistic effect.

So, the combination of 8 pg/ml anti-catalase with 8 pg/ml anti-SOD has the same effect as 2 ng/ml anti-catalase alone.

It was known from publications that catalase has an excellent and central role in the inhibition of the intercellular ROS-mediated signal pathways of tumor cells and in this way inhibits both the HOCl and the NO/peroxynitrite signal pathway. Inhibition or inactivation of the catalase has already been recognized as a way for the specific induction of apoptosis in tumor cells.

It is new and unexpected that also membranous SOD has a dominant and controlling function in the control of the ROS-mediated induction of apoptosis in tumor cells and that the inhibition of SOD by antibodies results in an efficient and specific ROS-mediated induction of apoptosis in tumor cells. This unexpected finding broadens the idea of the complexity of the control of the ROS signaling. It is seen that SOD and catalase in the control of both signal pathways complement each other very efficiently and complementary (see, FIG. 2). However, it is not readily apparent how the respective sole inhibition of SOD or catalase can result in an effective induction of apoptosis, since the complementary protecting mechanism should still always work. The key to the understanding of this situation is provided by the new findings represented here which show that the inhibition of one of the two protective partners by the increase in concentration of certain signal components inevitably results in the parallel inhibition of the complementary partners (see, FIGS. 5 and 6) and then, the signal pathways run unrestrained and can result in the apoptosis.

The present invention discloses a tumor therapy based on ROS signal pathways that could not be derived from the previously published findings.

It is new and unexpected that the combination of antibodies against SOD and catalase results in a very clear synergistic effect that leads to an extremely low demand for antibodies. In addition to the specific antitumor effect this additionally results in a financeable antibody-based tumor therapy.

It is the aim in the development of new drugs, active ingredients, or combinations of active ingredients that these act as specific as possible, so that only smallest amounts of active ingredient have to be administered. In this way, not only the costs can be kept low, but also the side effects will remain low. The present invention contributes to this purpose.

The invention claimed is:

1. A pharmaceutical composition, characterized in that it contains at least two antibodies or the biologically active fragments thereof, wherein a first of said at least two antibodies or fragments is directed against catalase and a second of said at least two antibodies or fragment is directed against superoxide dismutase.

2. The pharmaceutical composition according to claim 1, characterized in that the first of said at least two antibodies or fragments is directed against the catalytic center of the catalase.

3. The pharmaceutical composition according to claim 1, characterized in that the second of said at least two antibodies or fragments is directed against the catalytic center of the superoxide dismutase.

4. A method of treating a tumor disease comprising the step of administering the pharmaceutical composition according to claim 1 to a subject in need thereof.

5. The method according to claim 4, characterized in that the tumor disease is selected from the group consisting of carcinomas, lymphomas, Ewing's sarcomas, and neuroblastomas.

6. The method according to claim 5, characterized in that the tumor disease is a gastric carcinoma.

* * * * *

UNITED STATES PATENT AND TRADEMARK OFFICE
CERTIFICATE OF CORRECTION

PATENT NO. : 8,821,875 B2
APPLICATION NO. : 14/119177
DATED : September 2, 2014
INVENTOR(S) : Georg Bauer It is certified that error appears in the above-identified patent and that said Letters Patent is hereby corrected as shown below:

In The Specification

At column 9, line 67, replace the word "inhabitability" with -- inhibitability --.

At column 10, line 66, replace the word "inhabitability" with -- inhibitability --.

At column 12, line 58, replace the word "inhabitability" with -- inhibitability --.

Signed and Sealed this
Twenty-seventh Day of January, 2015

Michelle K. Lee
*Deputy Director of the United States Patent and Trademark Office*